United States Patent
Chu et al.

(10) Patent No.: US 11,664,090 B2
(45) Date of Patent: May 30, 2023

(54) BASECALLER WITH DILATED CONVOLUTIONAL NEURAL NETWORK

(71) Applicant: Life Technologies Corporation, Carlsbad, CA (US)

(72) Inventors: Yong Chu, Castro Valley, CA (US); Stephanie Jo Schneider, Mountain View, CA (US); Rylan Schaeffer, Mountain View, CA (US); David Woo, Foster City, CA (US)

(73) Assignee: Life Technologies Corporation, Carlsbad, CA (US)

(*) Notice: Subject to any disclaimer, the term of this patent is extended or adjusted under 35 U.S.C. 154(b) by 225 days.

(21) Appl. No.: 16/899,545

(22) Filed: Jun. 11, 2020

(65) Prior Publication Data

US 2021/0398615 A1   Dec. 23, 2021

(51) Int. Cl.
*G06K 9/62* (2022.01)
*G16B 30/00* (2019.01)
(Continued)

(52) U.S. Cl.
CPC .......... *G16B 30/00* (2019.02); *C12Q 1/6869* (2013.01); *G06K 9/6201* (2013.01); *G06K 9/623* (2013.01);
(Continued)

(58) Field of Classification Search
CPC ........ G16B 30/00; G16B 40/00; G16B 25/00; C12Q 1/6869; G06K 9/623; G06N 3/084; G06N 5/046
See application file for complete search history.

(56) References Cited

U.S. PATENT DOCUMENTS 11,538,556 B2   12/2022 Rothberg et al.
2009/0143995 A1*   6/2009 Dinauer ............... G16B 20/20
                                                    435/5
(Continued)

FOREIGN PATENT DOCUMENTS

WO   2004113557 A1   12/2004
WO   2019/147904 A1   8/2019
(Continued)

OTHER PUBLICATIONS

A. Graves, Chapter 2 Supervised Sequence Labelling, Supervised Sequence Labell. with Recur. Neur. Networks, 2012, pp. 5-13, SCI 385, Springer-Verlag, Berlin Heidelberg.
(Continued)

*Primary Examiner* — Edward Park
(74) *Attorney, Agent, or Firm* — Mauriel Kapouytian Woods LLP; Elaine K. Lee; Michael Mauriel

(57) ABSTRACT

A method of automatically sequencing or basecalling one or more DNA (deoxyribonucleic acid) molecules of a biological sample is described. The method comprises using a capillary electrophoresis genetic analyzer to measure the biological sample to obtain at least one input trace comprising digital data corresponding to fluorescence values for a plurality of scans. Scan labelling probabilities for the plurality of scans are generated using a trained artificial neural network comprising a plurality of layers including convolutional layers. A basecall sequence comprising a plurality of basecalls for the one or more DNA molecules based on the scan labelling probabilities for the plurality of scans is determined.

46 Claims, 12 Drawing Sheets

(51) Int. Cl.
  *G16B 40/00* (2019.01)
  *G16B 25/00* (2019.01)
  *C12Q 1/6869* (2018.01)
  *G06N 3/084* (2023.01)
  *G06N 5/046* (2023.01)
(52) U.S. Cl.
  CPC .......... *G06K 9/6256* (2013.01); *G06K 9/6277* (2013.01); *G06N 3/084* (2013.01); *G06N 5/046* (2013.01); *G16B 25/00* (2019.02); *G16B 40/00* (2019.02)

(56) References Cited

U.S. PATENT DOCUMENTS

| | | | |
|---|---|---|---|
| 2019/0197299 A1* | 6/2019 | Weng | G06N 3/08 |
| 2019/0348152 A1* | 11/2019 | Cao | G16B 30/00 |
| 2021/0012767 A1* | 1/2021 | Kupryjanow | G10L 15/20 |
| 2021/0295089 A1* | 9/2021 | Wang | G06K 9/628 |
| 2021/0406590 A1* | 12/2021 | Hu | G06N 3/0445 |

FOREIGN PATENT DOCUMENTS

| | | |
|---|---|---|
| WO | 2019147904 A1 | 8/2019 |
| WO | 2020123552 A1 | 6/2020 |

OTHER PUBLICATIONS

Jingwen Zeng, et al., Causalcall: Nanopore Basecalling Using a Temporal Convolutional Network, METHODS, Jan. 20, 2020, pp. 1-11, vol. 10, Article 1332, Frontiers in Genetics.

Alex Graves, et al., Towards End-to-End Speech Recognition with Recurrent Neural Networks, Proceedings of the 31st International Conference on Machine Learning, 2014, 9 pages, vol. 32, JMLR: W&CP, Beijing, China.

Brent Ewing, et al., Base-Calling of Automated Sequencer Traces Using Phred. II. Error Probabilities, Genome Research, 1998, pp. 186-194, vol. 8, Cold Spring Harbor Laboratory Press.

Shaojie Bai, et al., An Empirical Evaluation of Generic Convolutional and Recurrent Networks for Sequence Modeling, arXiv:1803.01271v2 [cs.LG], Apr. 19, 2018.

Omniyah G. Mohammed, et al., Novel algorithms for accurate DNA base-calling, J. Biomedical Science and Engineering, 2013, pp. 165-174, vol. 6.

Haotian Teng, et al., Chiron: translating nanopore raw signal directly into nucleotide sequence using deep learning, Technical Note, GigaScience, 2018, pp. 1-9, vol. 7.

Vladimir Boza, et al., DeepNano: Deep recurrent neural networks for base calling in MinION nanopore reads, PLOS ONE, Jun. 5, 2017, pp. 1-13, 12(6).

Marko Ratkovic, Deep Learning Model for Base Calling of MinION Nanopore Reads, Master Thesis Assignment No. 1417, Mar. 3, 2017, 48 pages, University of Zagreb.

Tianwei Yue, et al., Deep Learning for Genomics: A Concise Overview, School of Computer Science, May 8, 2018, 40 pages, Carnegie Mellon University, Pittsburgh, PA.

Matiur Rahman Minar, et al., Recent Advances in Deep Learning: An Overview, Department of Computer Science and Engineering, Jul. 21, 2018, Chittagong University of Engineering and Technology, Chittagong, Bangladesh.

Boža et al., "DeepNano: Deep Recurrent Neural Networks for Base Calling in MinION Nanopore Reads," PLOS ONE, vol. 12, No. 6, 2017, 13 pages.

Minar et al., "Recent Advances in Deep Learning: An Overview," 2018, 31 pages.

Mohammed et al., "Novel Algorithms for Accurate DNA Base-calling," Journal of Biomedical Science and Engineering, vol. 6, No. 2, 2013, pp. 165-174.

International Preliminary Report on Patentability issued in International Application No. PCT/US2019/065540 dated Jun. 8, 2021, 11 pages.

Ratković, "Deep Learning Model for Base Calling of MinION Nanopore Reads," Ph. D. thesis, University of Zagreb, 2017, 48 pages.

Teng et al., "Chiron: translating nanopore raw signal directly into nucleotide sequence using deep learning," GigaScience, vol. 7, No. 5, 2018, 9 pages.

Yue et al., "Deep Learning for Genomics: A Concise Overview," 2018, 40 pages.

Miculinć et al., "MinCall—MinION end2end convolutional deep learning basecaller," arXiv preprint arXiv:1904.10337, 2019, 8 pages.

"Sanger sequencing," Wikipedia, https://en.wikipedia.org/wiki/Sanger_sequencing, downloaded on Mar. 21, 2023, 7 pages.

Wang et al., "WaveNano: a signal-level nanopore base-caller via simultaneous prediction of nucleotide labels and move labels through bi-directional WaveNets," Quantitative Biology, 2018, vol. 6, 11 pages.

International Preliminary Report on Patentability issued in International Application No. PCT/US2021/036872 dated Dec. 22, 2022, 17 pages.

\* cited by examiner

BASECALLER WITH DILATED CONVOLUTIONAL NEURAL NETWORK

BACKGROUND

The present disclosure relates generally to systems, devices, and methods for basecalling, and more specifically to systems, devices, and methods for basecalling using deep learning for DNA sequencing analysis using capillary electrophoresis.

In capillary electrophoresis (CE), a biological sample, such as a nucleic acid sample, is injected at the inlet end of the capillary, into a denaturing separation medium in the capillary, and an electric field is applied to the capillary ends. The different nucleic acid components in a sample, e.g., a polymerase chain reaction (PCR) mixture or other sample, migrate to the detector point with different velocities due to differences in their electrophoretic properties. Consequently, they reach the light detector (usually a fluorescence detector operating in the visible light range or an ultraviolet (UV) absorbance detector) at different times. Results present as a series of detected peaks, where each peak represents ideally one nucleic acid component or species of the sample.

The magnitude of any given peak, including an artifact peak, is most often determined optically on the basis of either UV absorption by nucleic acids, e.g., DNA, or by fluorescence emission from one or more labelled dyes associated with the nucleic acid. UV and fluorescence detectors applicable to nucleic acid CE detection are well known in the art.

CE capillaries themselves are frequently quartz, although other materials known to those of skill in the art can be used. There are a number of CE systems available commercially, having both single and multiple-capillary capabilities. The methods described herein are applicable to any device or system for denaturing CE of nucleic acid samples.

Historically, Sanger sequencing with capillary electrophoresis (CE) genetic analyzers has been considered the gold-standard DNA sequencing technology. It provides a high degree of accuracy, long-read capabilities, and the flexibility to support a diverse range of applications in many research areas. The accuracies of basecalls and quality values (QVs) for Sanger sequencing on CE genetic analyzers are considered essential for successful sequencing projects. Legacy basecallers were previously developed to provide a complete and integrated basecalling solution to support sequencing platforms and applications and were originally engineered to basecall long plasmid clones (pure bases) and then extended later to basecall mixed base data to support variant identification.

However, obvious mixed bases are occasionally called as pure bases even with high predicted QVs, and false positives, in which pure bases are incorrectly called as mixed bases, also occur relatively frequently due to sequencing artefacts such as dye blobs, n−1 peaks due to polymerase slippage and primer impurities, mobility shifts, etc. Clearly, the basecalling and QV accuracy for mixed bases need to be improved to support sequencing applications for identifying variants such as Single Nucleotide Polymorphisms (SNPs) and heterozygous insertion deletion variants (het indels). The basecalling accuracy of legacy basecallers at 5' and 3' ends is also relatively low due to mobility shifts and low resolution at 5' and 3' ends. Legacy basecallers may also struggle to basecall amplicons shorter than 150 base pairs (bps) in length, particularly shorter than 100 bps, failing to estimate average peak spacing, average peak width, spacing curve, and/or width curve, sometimes resulting in increased error rate.

Therefore, improved basecalling accuracy for pure and mixed bases, especially at 5' and 3' ends is also very desirable so that basecalling algorithms can deliver higher fidelity of Sanger sequencing data, improve variant identification, increase read length, and also save sequencing costs for sequencing applications.

Recent basecallers frequently use recurrent neural network-based models to identify the basecalling sequence based on raw input data. With the recurrent structures, the recurrent neural networks can properly model the time-series data in basecalling, but as the computation of one time point must wait for the result of earlier time points, the speed of basecallers based on recurrent networks may be severely restricted, particularly when dealing with longer sequencing reads.

SUMMARY

Systems and methods are described for use in capillary electrophoresis deep learning based basecalling, such as in convolutional neural network-based basecalling systems utilizing capillary electrophoresis genetic analyzers based on microfluidic separations (in which separation is performed through micro-channels etched into or onto glass, silicon or other substrate), or separation through capillary electrophoresis using single or multiple cylindrical capillary tubes.

Convolutional architectures, such as dilated convolutional neural networks implemented in embodiments of the present invention described herein, may perform well in genetic sequence modeling tasks and outperform recurrent networks, and reach state-of-the-art accuracy in a broad range of sequence modeling tasks. The training and inference of convolutional neural networks is much faster than for recurrent networks such as long short term memory (LSTM) networks. Dilated convolutional neural networks in particular, may achieve an exponentially large receptive field with fewer parameters and fewer layers.

A method of automatically basecalling one or more DNA (deoxyribonucleic acid) molecules of a biological sample is described. The method comprises converting a plurality of fluorescent signals of the biological sample, wherein each of the plurality of fluorescent signals is measured by a capillary electrophoresis genetic analyzer, to at least one input trace comprising digital data corresponding to fluorescent values at a plurality of scans. Scan labelling probabilities for each of the plurality of scans are generated. The scan labelling probabilities are generated using a trained deep neural network comprising a plurality of layers including convolutional layers. A basecall sequence comprising a plurality of basecalls for the one or more DNA molecules based on the one or more scan labelling probabilities for each of the plurality of scans is determined.

In some embodiments, a basecall position for each basecall in a basecall sequence is also determined, where the basecall position corresponds to a scan position of a peak scan labelling probability associated with the basecall. In some embodiments, searching for the peak probability associated with a given basecall is made more efficient by first identifying a first and last scan in a scan range of scans corresponding to scan labelling probabilities associated with the given basecall and then only searching within that scan range.

In some embodiments a quality value for each basecall is determined using feature values derived from the scan probability values associated with that basecall rather than using values of the image trace associated with the basecall. In addition, in some embodiments of the present invention a neural network is trained to call mixed bases of 2 bases per basecall position. In some embodiments, a neural network may be trained to call mixed bases of greater than 2 bases per basecall position.

Figure 1:
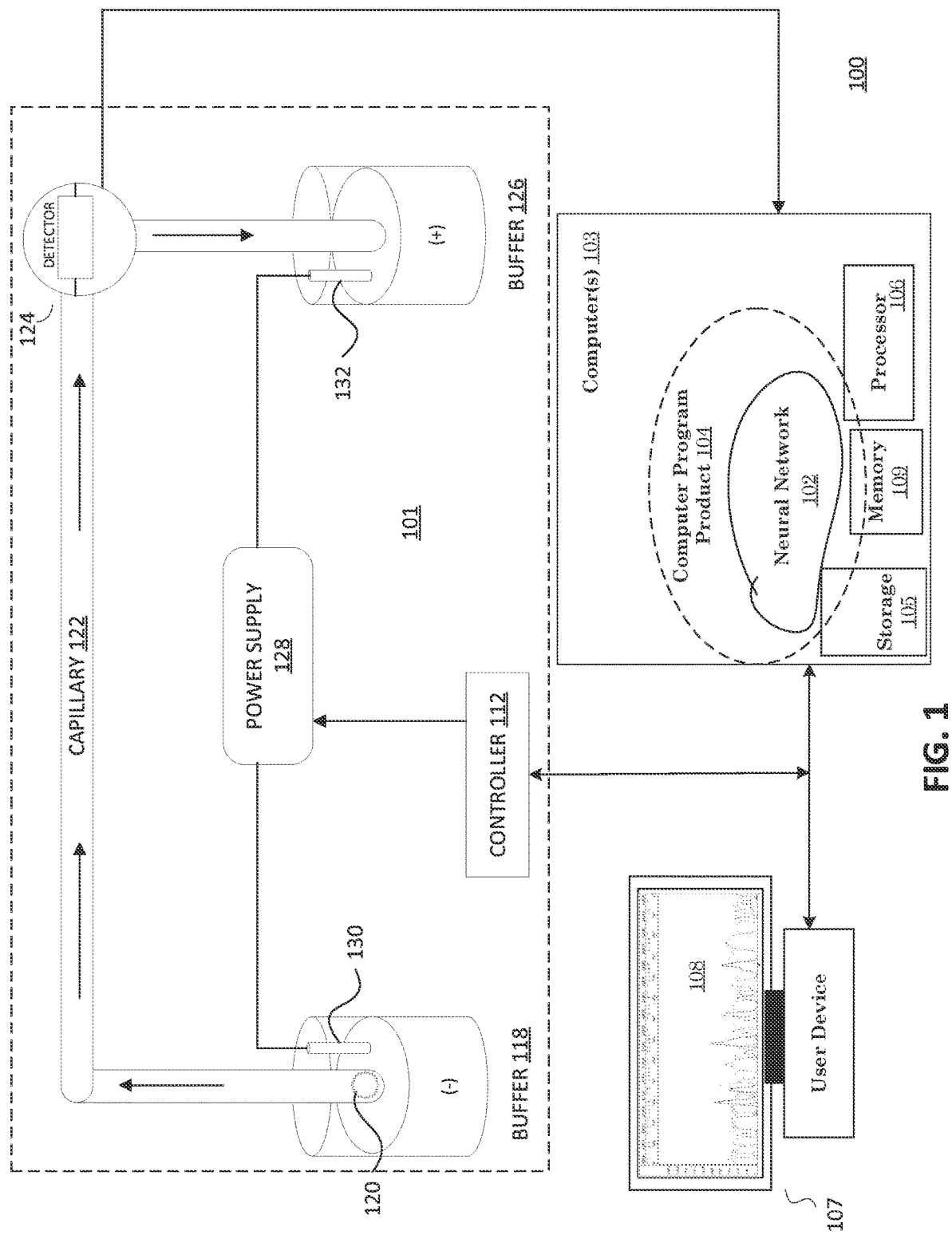
FIG. 1 illustrates a capillary electrophoresis sequencing system in accordance with an embodiment of the present invention.

While the invention is described with reference to the above drawings, the drawings are intended to be illustrative, and other embodiments are consistent with the spirit, and within the scope, of the invention.

DETAILED DESCRIPTION

The various embodiments now will be described more fully hereinafter with reference to the accompanying drawings, which form a part hereof, and which show, by way of illustration, specific examples of practicing the embodiments. This specification may, however, be embodied in many different forms and should not be construed as limited to the embodiments set forth herein; rather, these embodiments are provided so that this specification will be thorough and complete, and will fully convey the scope of the invention to those skilled in the art. Among other things, this specification may be embodied as methods or devices. Accordingly, any of the various embodiments herein may take the form of an entirely hardware embodiment, an entirely software embodiment or an embodiment combining software and hardware aspects. The following specification is, therefore, not to be taken in a limiting sense.

This patent application contains material related to PCT Application No. PCT/US2019/065540, filed on Dec. 10, 2019, with a priority date of Dec. 10, 2018, which is hereby incorporated by reference herein in its entirety. This and other technical publications, patent publications, scientific publications, and all other extrinsic materials discussed herein are incorporated by reference in their entirety.

Embodiments of the present invention discussed herein utilize principles of DNA replication used in Sanger dideoxy sequencing. This process takes advantage of the ability of DNA polymerase to incorporate 2',3'-dideoxynucleotides—nucleotide base analogs that lack the 3'-hydroxyl group essential in phosphodiester bond formation.

Sanger dideoxy sequencing requires a DNA template, a sequencing primer, DNA polymerase, deoxynucleotides (dNTPs), dideoxynucleotides (ddNTPs), and reaction buffer. As Sanger dideoxy sequencing was originally designed, four separate reactions are set up, each containing radioactively labeled nucleotides and either ddA, ddC, ddG, or ddT. The annealing, labeling, and termination steps are performed on separate heat blocks. DNA synthesis is performed at 37° C., the temperature at which DNA polymerase has the optimal enzyme activity. DNA polymerase adds a deoxynucleotide or the corresponding 2',3'-dideoxynucleotide at each step of chain extension. Whether a deoxynucleotide or a dideoxynucleotide is added depends on the relative concentration of both molecules. When a deoxynucleotide (A, C, G, or T) is added to the 3' end, chain extension can continue. However, when a dideoxynucleotide (ddA, ddC, ddG, or ddT) is added to the 3' end, chain extension terminates. Sanger dideoxy sequencing results in the formation of extension products of various lengths terminated with dideoxynucleotides at the 3' end.

The extension products are then separated by electrophoresis. During electrophoresis, an electrical field is applied so that the negatively charged DNA fragments move toward the positive electrode. The speed at which a DNA fragment moves through the medium is inversely proportional to its molecular weight. This process of electrophoresis can separate the extension products by size at a resolution of one base.

As used in embodiments of the present invention, an automated DNA fluorescence-based cycle sequencing system manufactured and used by Applied Biosystems, Inc., is an extension and refinement of Sanger dideoxy sequencing. Applied Biosystems automated DNA sequencing generally follows the flow of DNA template preparation, cycle sequencing, purification after cycle sequencing, capillary electrophoresis, and data analysis. Exemplary fluorescence-based cycle sequencing systems that may be used in embodiments of the present invention are further described in "DNA Sequencing by Capillary Electrophoresis Chemistry Guide ($3^{rd}$ Edition, 2016) published by Thermo Fisher Scientific, Inc., which is incorporated by reference herein in its entirety.

Like Sanger sequencing, fluorescence-based cycle sequencing requires a DNA template, a sequencing primer, a thermal stable DNA polymerase, deoxynucleoside triphosphates/deoxynucleotides (dNTPs), dideoxynucleoside triphosphates/deoxynucleotides (ddNTPs), and buffer. But unlike Sanger's method, which uses radioactive material, cycle sequencing uses fluorescent dyes to label the extension products, and the components are combined in a reaction that is subjected to cycles of annealing, extension, and denaturation in a thermal cycler. Thermal cycling the sequencing reactions creates and amplifies extension products that are terminated by one of the four dideoxynucleotides. The ratio of deoxynucleotides to dideoxynucleotide is optimized to produce a balanced population of long and short extension products.

Automated cycle sequencing procedures used in some embodiments of the present invention incorporate fluorescent dye labels using dye-labeled dideoxynucleotide (dye terminators) using four different dyes. Because each dye emits a unique wavelength when excited by light, the fluorescent dye on the extension product identifies the 3' terminal dideoxynucleotide as A, C, G, or T.

With dye terminator chemistry, each of the four dideoxynucleotide terminators is tagged with a different fluorescent dye. One reaction is performed, containing the enzyme, nucleotides, and all dye-labeled dideoxynucleotides. The products from this reaction are injected into one capillary.

In one embodiment of the invention, the cycle sequencing reaction is directed by highly modified, thermally stable DNA polymerases, selected to allow incorporation of dideoxynucleotides, to process through stretches of G-C-rich and other difficult sequences, and to produce peaks of varying heights. The modified DNA polymerases are also formulated with a pyrophosphatase to prevent reversal of the polymerization reaction (pyrophosphorolysis).

In one embodiment of the present invention, Applied Biosystems Cycle Sequencing Kits available for dye terminator chemistries include: BigDye Terminator v1.1 and v3.1 Cycle Sequencing Kits, dGTP BigDye Terminator v1.0 and v3.0 Cycle Sequencing Kits, and BigDye Direct Cycle Sequencing Kits. The fluorescent dyes used in BigDye terminators, BigDye primers, and BigDye Direct have narrower emission spectra and less spectral overlap than the rhodamine dyes used in previous sequencing kits. As a result, the dyes may tend to produce less noise.

Historically, DNA sequencing products were separated using polyacrylamide gels that were manually poured between two glass plates. Capillary electrophoresis using a denaturing flowable polymer has largely replaced the use of gel separation techniques due to significant gains in workflow, throughput, and ease of use. Fluorescently labeled DNA fragments are separated according to molecular weight. Because there is no need to pour gels with capillary electrophoresis, DNA sequence analysis using CE is automated more easily and can process more samples at once.

During capillary electrophoresis, the extension products of the cycle sequencing reaction enter the capillary as a result of electrokinetic injection. A high voltage charge applied to the buffered sequencing reaction forces the negatively charged fragments into the capillaries. The extension products are separated by size based on their total charge. The electrophoretic mobility of the sample can be affected by the run conditions: the buffer type, concentration, and pH, the run temperature, the amount of voltage applied, and the type of polymer used.

Shortly before reaching the positive electrode, the fluorescently labeled DNA fragments, separated by size, move across the path of a laser beam. The laser beam causes the dyes on the fragments to fluoresce. In one embodiment of the invention, an optical detection device on Applied Biosystems genetic analyzers and/or DNA analyzers detects the fluorescence. Data collection software used in one embodiment of the invention converts the fluorescent signal to digital data, then records the data in an AB1 (.ab1) file. Because each dye emits light at a different wavelength when excited by the laser, all four colors, and therefore all four bases, can be detected and distinguished in one capillary injection.

FIG. 1 illustrates System 100 in accordance with an exemplary embodiment of the present invention. System 100 comprises capillary electrophoresis ("CE") instrument 101, one or more computers 103, and user device 107.

Referencing FIG. 1, a CE instrument 101 in one embodiment comprises a source buffer 118 containing buffer and receiving a fluorescently labeled sample 120, a capillary 122, a destination buffer 126, a power supply 128, and a controller 112. The source buffer 118 is in fluid communication with the destination buffer 126 by way of the capillary 122. The power supply 128 applies voltage to the source buffer 118 and the destination buffer 126 generating a voltage bias through an anode 130 in the source buffer 118 and a cathode 132 in the destination buffer 126. The voltage applied by the power supply 128 is configured by a controller 112 operated by the computing device 103. The fluorescently labeled sample 120 near the source buffer 118 is pulled through the capillary 122 by the voltage gradient, and optically labeled nucleotides of the DNA fragments within the sample are detected as they pass through an optical sensor 124 on the way to destination buffer 126. Differently sized DNA fragments within the fluorescently labeled sample 120 are pulled through the capillary at different times due to their size.

The optical sensor 124 detects the fluorescent labels on the nucleotides as an image signal and communicates the image signal to the computing device 103. The computing device 103 aggregates the image signal as sample data and utilizes a basecaller computer program product 104 to operate a deep neural network 102 to transform the sample data into processed data, including a basecall sequence and quality values, and generate an electropherogram that may be shown on a display 108 of user device 107.

Instructions for implementing deep neural network 102 reside on computing device 103 in computer program product 104 which is stored in storage 105 and those instructions are executable by processor 106. When processor 106 is executing the instructions of computer program product 104, the instructions, or a portion thereof, are typically loaded into working memory 109 from which the instructions are readily accessed by processor 106. In one embodiment, computer program product 104 is stored in storage 105 or another non-transitory computer readable medium (which may include being distributed across media on different devices and different locations). In alternative embodiments, the storage medium is transitory.

In one embodiment, processor 106 in fact comprises multiple processors which may comprise additional working memories (additional processors and memories not individually illustrated) including a graphics processing unit (GPU) comprising at least thousands of arithmetic logic units supporting parallel computations on a large scale. GPUs are often utilized in deep learning applications because they can perform the relevant processing tasks more efficiently than can typical general-purpose processors (CPUs). Other embodiments comprise one or more specialized processing units comprising systolic arrays and/or other hardware arrangements that support efficient parallel processing. In some embodiments, such specialized hardware works in conjunction with a CPU and/or GPU to carry out the various processing described herein. In some embodiments, such specialized hardware comprises application specific integrated circuits and the like (which may refer to a portion of an integrated circuit that is application-specific), field programmable gate arrays and the like, or combinations thereof. In some embodiments, however, a processor such as processor 106 may be implemented as one or more general purpose processors (preferably having multiple cores) without necessarily departing from the spirit and scope of the present invention.

User device 107 incudes a display 108 for displaying results of processing carried out by neural network 102. In alternative embodiments, a neural network such as neural network 102, or a portion of it, may be stored in storage devices and executed by one or more processors residing on CE instrument 101 and/or user device 107. Such alternatives do not depart from the scope of the invention.

Figure 2:
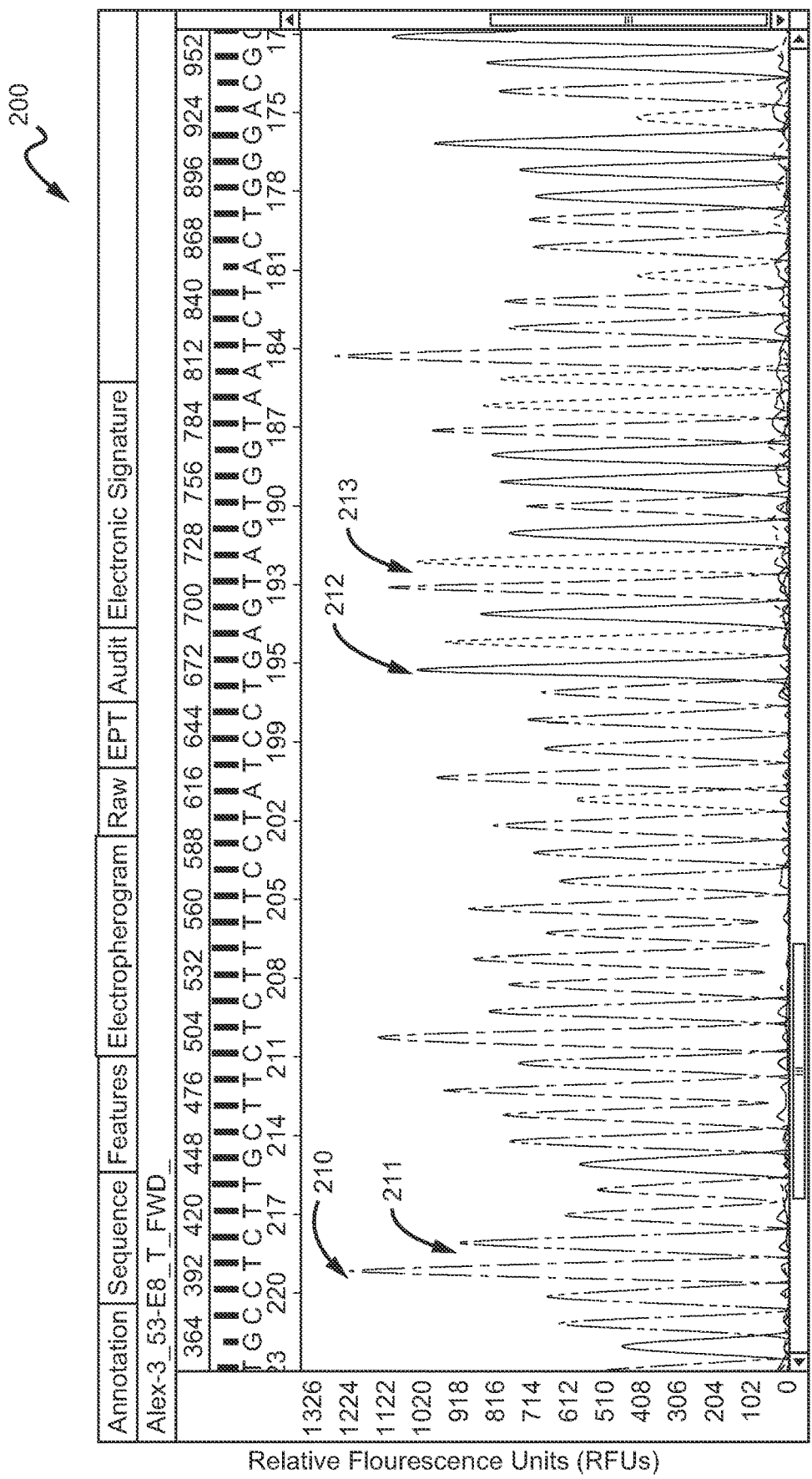
FIG. 2 illustrates an exemplary electropherogram that may be displayed in accordance with an embodiment of the present invention.

FIG. 2 illustrates an exemplary electropherogram 200 that may be displayed in accordance with an embodiment of the present invention. Electropherogram 200 includes a graph (with a y-axis of the relative fluorescence units (RFUs), and an x-axis of the scan), which displays the image signal of detected fluorescent labels on the nucleotides as a sequence of peaks, e.g., 210, 211, 212 and 213. The signals corresponding to the fluorescently labelled nucleotides may be displayed in four different colors, which may be represented in FIG. 2, and in other figures herein either in color, or in grayscale or as different variations of black and white hatched lines representing the various colors. Each color represents a base (e.g., in IUPAC-IUB notation T=red, C=blue, G=black, A=green, respectively) called for that peak. Two or more (e.g., 3 or 4) peaks may also occur in one position, in which case a mixed base may be called (e.g., mixed bases of 2 peaks may be expressed in IUPAC-IUB notation as follows: A+C=M, A+G=R, A+T=W, C+G=S, C+T=Y, G+T=K).

Figure 3:
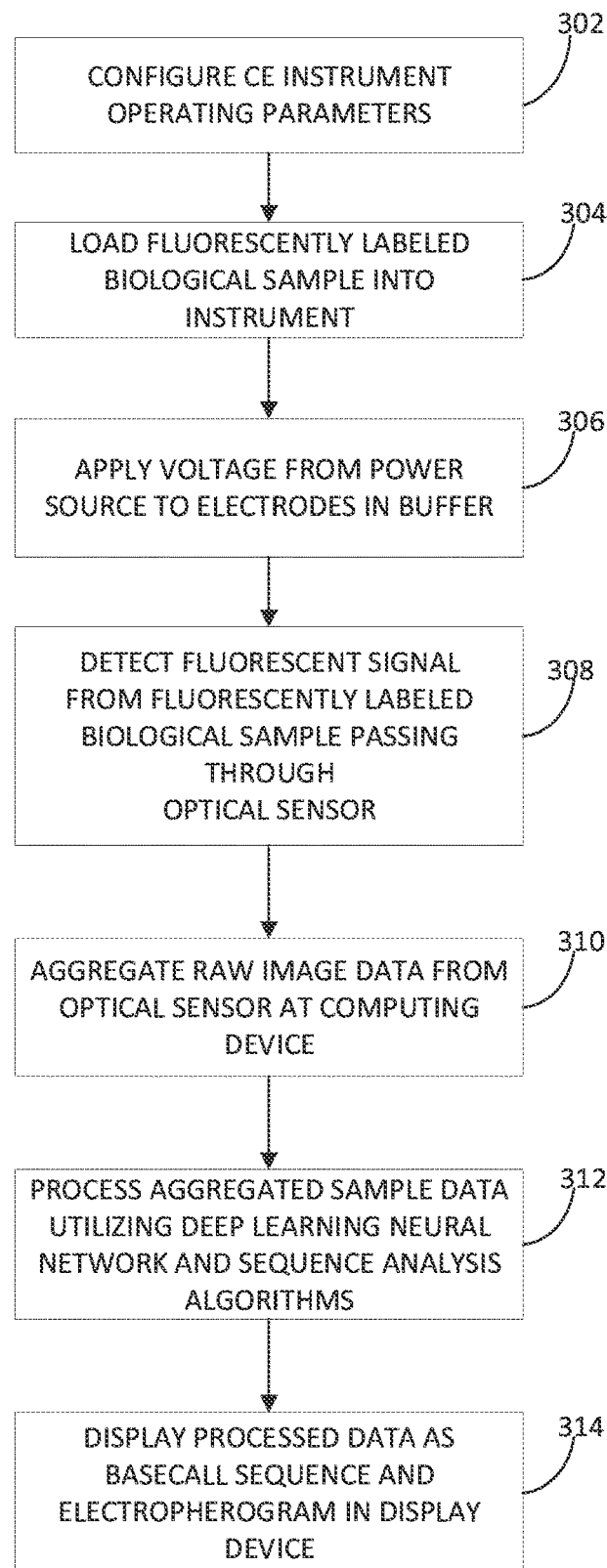
FIG. 3 illustrates a capillary electrophoresis genetic analysis process in accordance with some embodiments of the present invention.

Referencing FIG. 3, a CE process 300 utilized in one embodiment of the present invention involves configuring capillary electrophoresis instrument operating parameters to sequence at least one fluorescently labeled sample (block 302). The configuration of the instrument may include creating or importing a plate setting for running a series of samples and assigning labels to the plate samples to assist in the processing of the collected imaging data. The process may also include communicating configuration controls to a controller to start applying voltage at a predetermined time. In block 304, the CE process 300 loads the fluorescently labeled sample into the instrument. After the sample is loaded into the instrument, the instrument may transfer the sample from a plate well into the capillary tube and then position the capillary tube into the starting buffer at the beginning of the capillary electrophoresis process. In block 306, the CE process 300 begins the instrument run after the sample has been loaded into the capillary by applying a voltage to the buffer solutions positioned at opposite ends of the capillary, forming an electrical gradient to transport DNA fragments of the fluorescently labeled sample from the starting buffer to a destination buffer and traversing an optical sensor. In block 308, the CE process 300 detects the individual fluorescent signals on the nucleotides of the DNA fragments as they move towards the destination buffer through the optical sensor and communicates the image signal to the computing device. In block 310, the CE process 300 aggregates the image signal at the computing device from the optical sensor, analyzes the aggregated image signals, and generates sample data that corresponds to the fluorescent intensity of the nucleotides of the DNA fragments. In block 312, the CE process 300 processes the sample data through the utilization of both a deep learning neural network and sequence analysis algorithms to help identify the bases called in the DNA fragments at the particular time point (which will correspond to a particular scan number in a plurality of scans). In block 314, the CE process 300 displays processed data as an analyzed trace displayed in an electropherogram and a basecall sequence on a display device.

Figure 4:
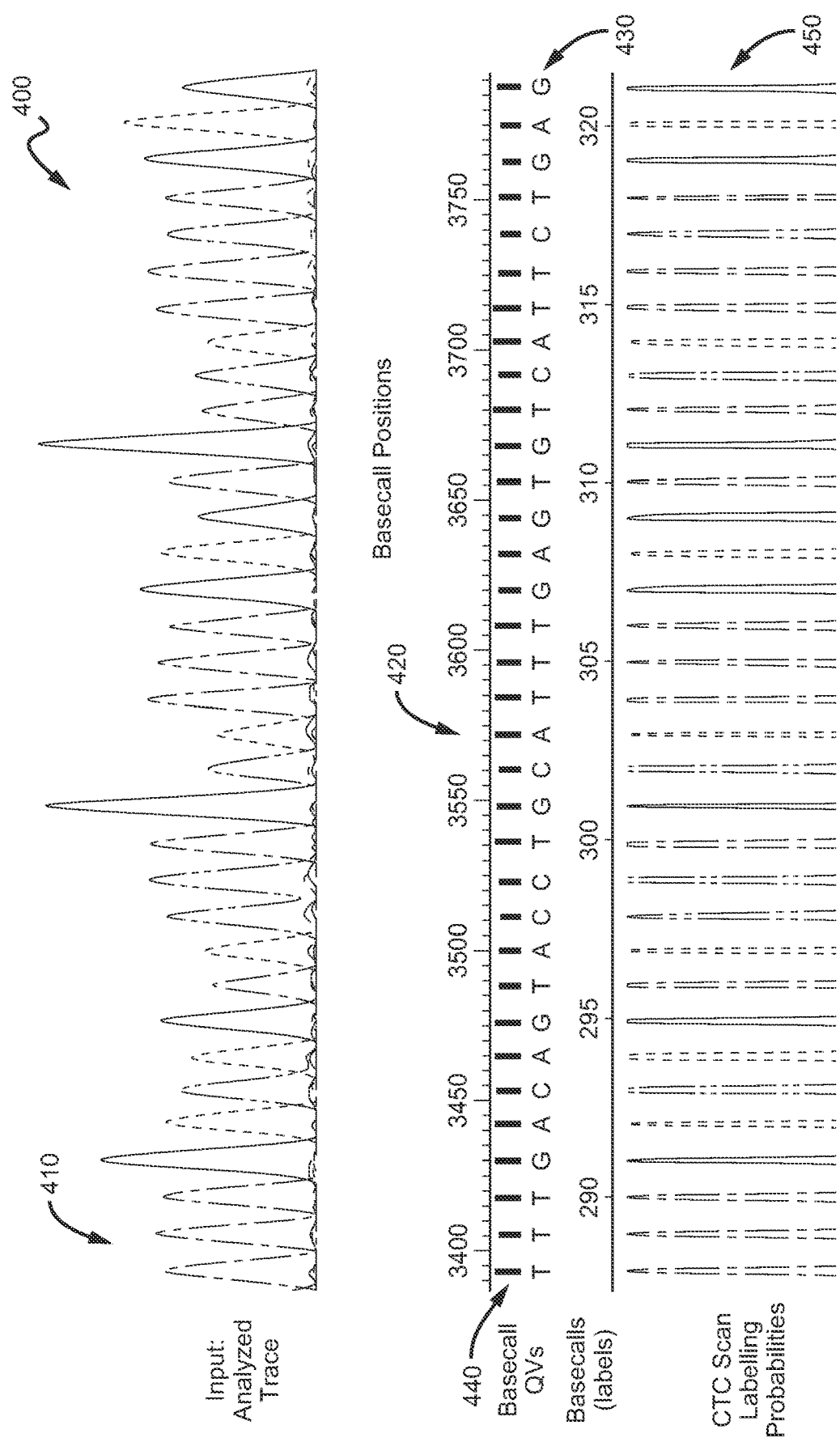
FIG. 4 illustrates a diagram of exemplary input and output data that may be displayed in accordance with an embodiment of the present invention.

FIG. 4 illustrates a diagram of exemplary input and output data 400 that may be produced and/or displayed in accordance with an embodiment of the present invention. Input data comprises an analyzed trace 410 produced using CE process 300 which may be displayed in an electropherogram similar to that shown in FIG. 2. Output data comprises a plurality of basecall positions 420, a plurality of basecall labels 430, and a plurality of quality values 440. FIG. 4 also shows intermediate data CTC scan labelling probabilities 450 corresponding to each basecall that comprises an output of the dilated convolutional neural network described below and implemented in embodiments of the present invention described herein. In particular embodiments, CTC scan labelling probabilities are generally not displayed in electropherogram 200 of FIG. 2, although the basecall positions 420, basecall labels 430, and quality values 440 are generally displayed in a typical embodiment.

In some embodiments of the invention, the user may select whether their input data contains pure bases only, or contains mixed bases. Basecalling is the interpretation of the dye data that is used to draw the electropherogram. This determines which nucleotide (represented by basecall label 430) belongs at which position (represented by basecall position 420). Each color shown in the input analyzed trace 410 and basecall label 430 represents a base (may be rendered here in grayscale and/or different/distinct dotted/dashed lines for each base instead of in the standard color notation. In FIG. 4, input analyzed trace 410 and basecall labels 430 are rendered in the colors T=red, C=blue, G=black, A=green, respectively called for each peak. As discussed above, a basecall could also be a mixture of two or more (e.g., three or four) nucleotides showing two or more peaks that are superimposed on each other or shifted slightly from each other, and possibly of different peak heights.

A quality value 440 in FIG. 4 is also generated for each basecall in embodiments of the present invention. Quality value 440 is shown in FIG. 4 output data 400 as a vertical bar of varying height for each called base 430 called depending on a computed estimated probability of error or quality value. A quality value computation implemented in embodiments of the present invention is described further in this specification.

Figure 5:
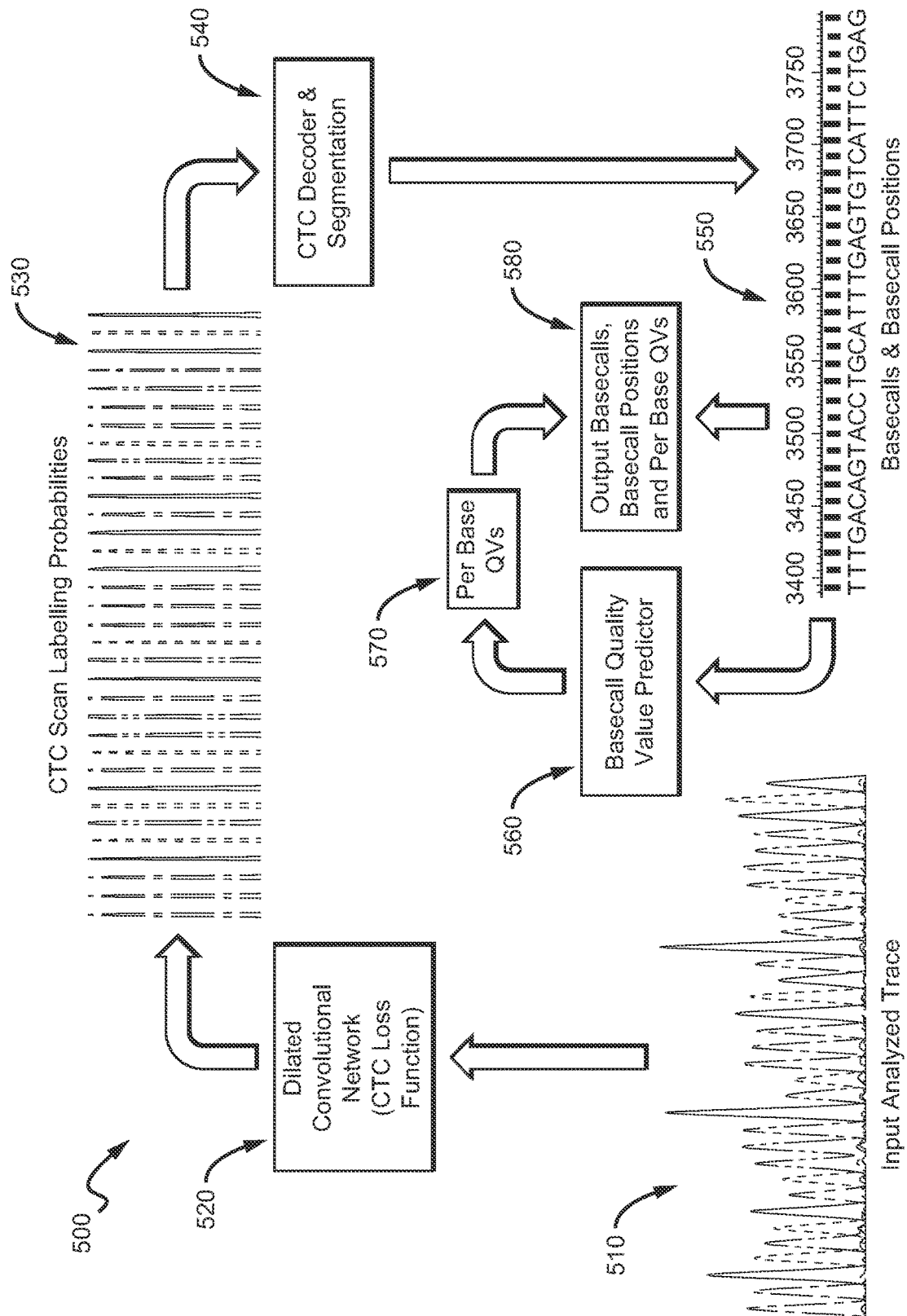
FIG. 5 illustrates a deep learning based basecalling workflow process in accordance with an embodiment of the present invention.

FIG. 5 illustrates a diagram for a deep basecalling workflow process 500 in accordance with an embodiment of the present invention. Input data comprises an analyzed trace 510 produced using CE process 300 which may be displayed in an electropherogram similar to that shown in FIG. 2. The input trace 510 may be a sequence of dye RFUs collected from a capillary electrophoresis (CE) instrument, or raw spectrum data collected in the CE instrument directly. Input trace 510 may be divided into a number of windows, each comprising a plurality of scans. In one embodiment of the invention, a scan window size determines the number of scans to the scan labelling model 520.

The scan labelling model 520 receives the input scan window and generates scan labelling probabilities for all scans in the scan window. The scan labelling model 520 may comprise one or more trained models. The models may be selected to be utilized to generate the scan labelling probabilities. A deep learning model comprising a neural network 520 is trained to learn an optimal mapping function from analyzed trace 510 to scan labelling probabilities 530 in one embodiment of the present invention. In one embodiment of the present invention, the neural network 520 comprises a dilated convolutional neural network trained to minimize a loss between a target sequence of bases and the corresponding predicted scan labelling probabilities 530 using a Connectionist Temporal Classification (CTC) loss function as described further herein in this specification below. The deep learning model may be trained in accordance with the process depicted in FIG. 10.

The decoder 540 receives the scan labelling probabilities for the assembled scan windows. The decoder 540 then decodes the scan labelling probabilities into basecalls for the input trace sequence. The decoder 540 may utilize a prefix beam search or other decoders on the assembled label probabilities to find the basecalls for the sequencing sample.

The CTC scan labelling probabilities 530 are decoded using CTC decoder and segmentation module 540, which walks through scan labelling probabilities 530 for all scans to generate a sequence with a maximum labelling probability as a final result. CTC decoder and segmentation module 540 also finds a scan range and then the scan position of a peak labelling probability within the scan range for each called base to generate basecalls (labels) and basecall positions 550 for the sequence. Output data generated by CTC decoder and segmentation module 540 is then used by Basecall Quality Value (QV) Predictor 560 to calculate Quality Values (QVs) 570, a quality score for each called base as described further herein in this specification below. Basecall QV Predictor 560 finds a quality score for each called base from a trained QV lookup table by using features calculated from CTC scan labelling probabilities as a key.

Dilated Convolutional Neural Network

Recent research indicates that convolutional neural network architectures can outperform recurrent neural networks and reach state-of-the-art accuracy in audio synthesis, word-level language modeling, and machine translation. For example, a generic temporal convolutional network (TCN) architecture as described in the following reference: Bai, Shaojie, Kolter, J. Zico and Koltun, Vladlen, An Empirical Evaluation of Generic Convolutional and Recurrent Networks for Sequence Modeling, arXiv:1803.01271v2 [cs.LG], 19 Apr. 2018 ("Bai et al.") has been evaluated across a broad range of sequence modeling tasks other than Sanger sequencing using CE, such as polyphonic music modeling, word-level sequence modeling, and character-level sequence modeling. The results of Bai et al. indicate that TCN outperforms canonical recurrent networks such as LSTMs while demonstrating longer effective memory.

Embodiments of the present invention utilize a neural network architecture similar to TCN but, in the case of some embodiments, the neural network architecture utilized has some important distinctions. In one embodiment of the present invention, the network architecture differs from TCN in that 1D fully dilated convolutions were used instead of 1D fully dilated causal convolutions. TCN uses causal convolutions, where an output at time t is convolved only with elements from time t and earlier in the previous layer. However, in CE basecalling, since the entire input scan trace is available during basecalling, past, current and future scan data may be exploited. Some embodiments of the present invention utilize a one-dimensional non-causal fully dilated convolutional network, where an output at time t is convolved not only with elements from time t and earlier but also with later elements in the previous layer, and the length of subsequent layers is the same as the previous layers with zero padding added. In one embodiment of the invention, dilated convolutions are used to achieve an exponentially large receptive field with fewer parameters and fewer layers.

Figure 6:
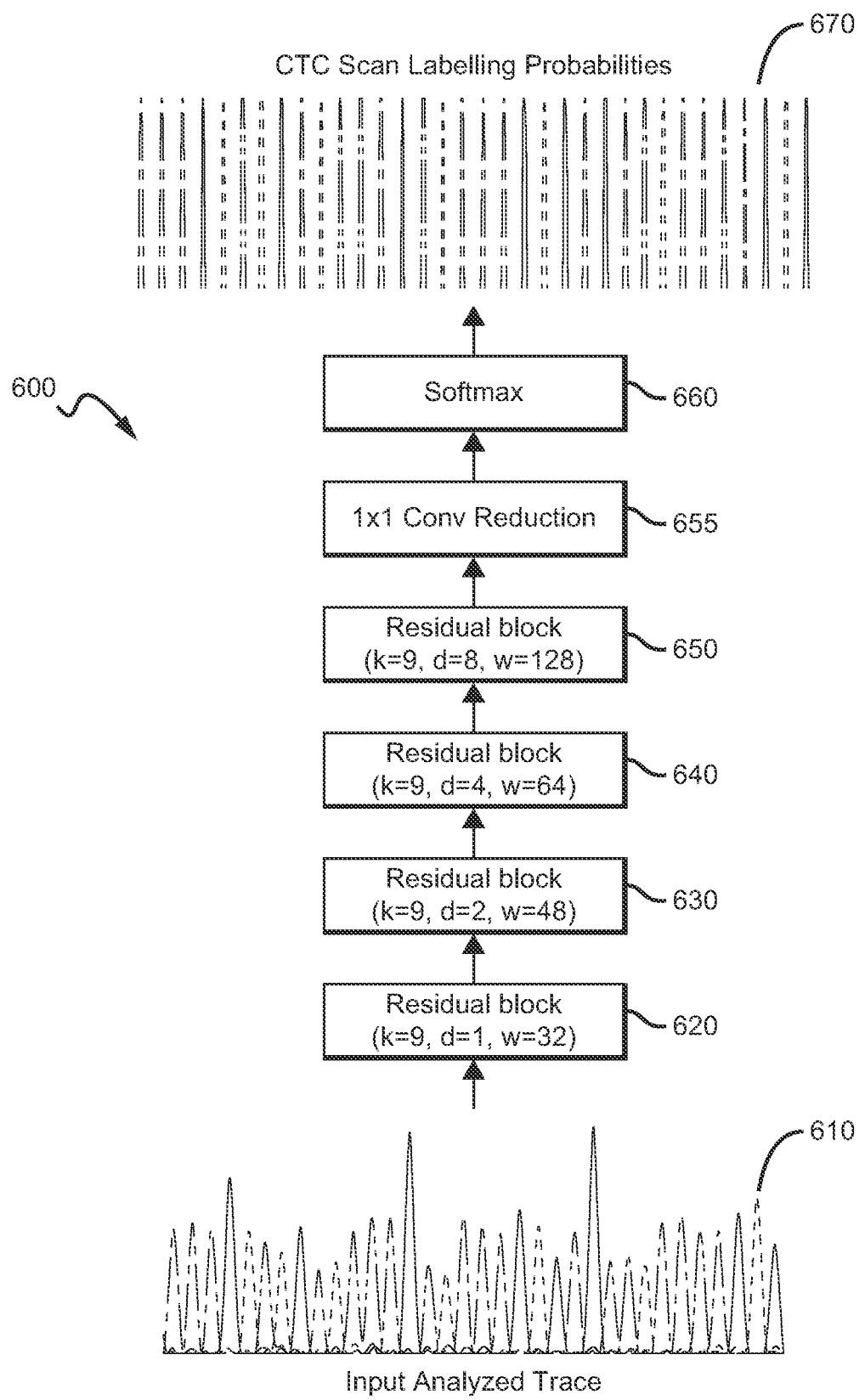
FIG. 6 illustrates a deep neural network architecture in accordance with an embodiment of the present invention.

FIG. 6 illustrates a deep neural network architecture 600 in accordance with an embodiment of the present invention. In the embodiment shown in FIG. 6, deep neural network architecture 600 is trained to learn an optimal mapping function from an input analyzed trace 610 to output of scan labelling probabilities 670.

Input analyzed trace 610 may comprise a plurality of scans which segment a plurality of fluorescent signals of input analyzed trace 610. As the rate of DNA movement may be unstable and slower than the rate of measurement of the fluorescent signals, the base sequences may differ in length and be much shorter than the segments of fluorescent signal measurements. Thus, the main task of the model is to transform the scans of fluorescent signal measurements with fixed length T into base sequences with non-uniform length M ($0<M<T$).

Network architecture 600 comprises a plurality of hidden layers, included in each of four residual blocks, shown as blocks 620, 630, 640, and 650, where each residual block comprises one or more non-causal convolutional layers. In one embodiment of the invention, a filter size k=9 for all residual blocks 620-650 is used. The dilation factors for each residual block are given in one embodiment of the invention as $d=2^{(i-1)}$ where i is the depth of the residual block in the neural network, where i=1, 2, 3, and 4 for residual blocks 620, 630, 640, and 650 respectively. The feature map sizes are given as w=32, 48, 64, and 128 for residual blocks 620, 630, 640, and 650 respectively. The stacked residual blocks act as a feature extractor to map fluorescent signal measurements to feature space. As the dilated non-causal convolution is implemented in the time dimension in some embodiments of the present invention, the extracted features indicate the correlation of the fluorescent signal measurements at different time points. Subsequently, a 1×1 convolutional reduction layer 655 is added after the last residual block to reduce the number of extracted features to match the number of output labels, and a softmax function layer 660 is added after the 1×1 convolutional reduction layer. In one embodiment of the invention, softmax function 660 transforms the output of the 1×1 convolution reduction layer 655 into a matrix of probabilities, in which each matrix row indicates the probabilities of bases appearing at that time point to generate the plurality of scan labelling probabilities 670.

Figure 7:
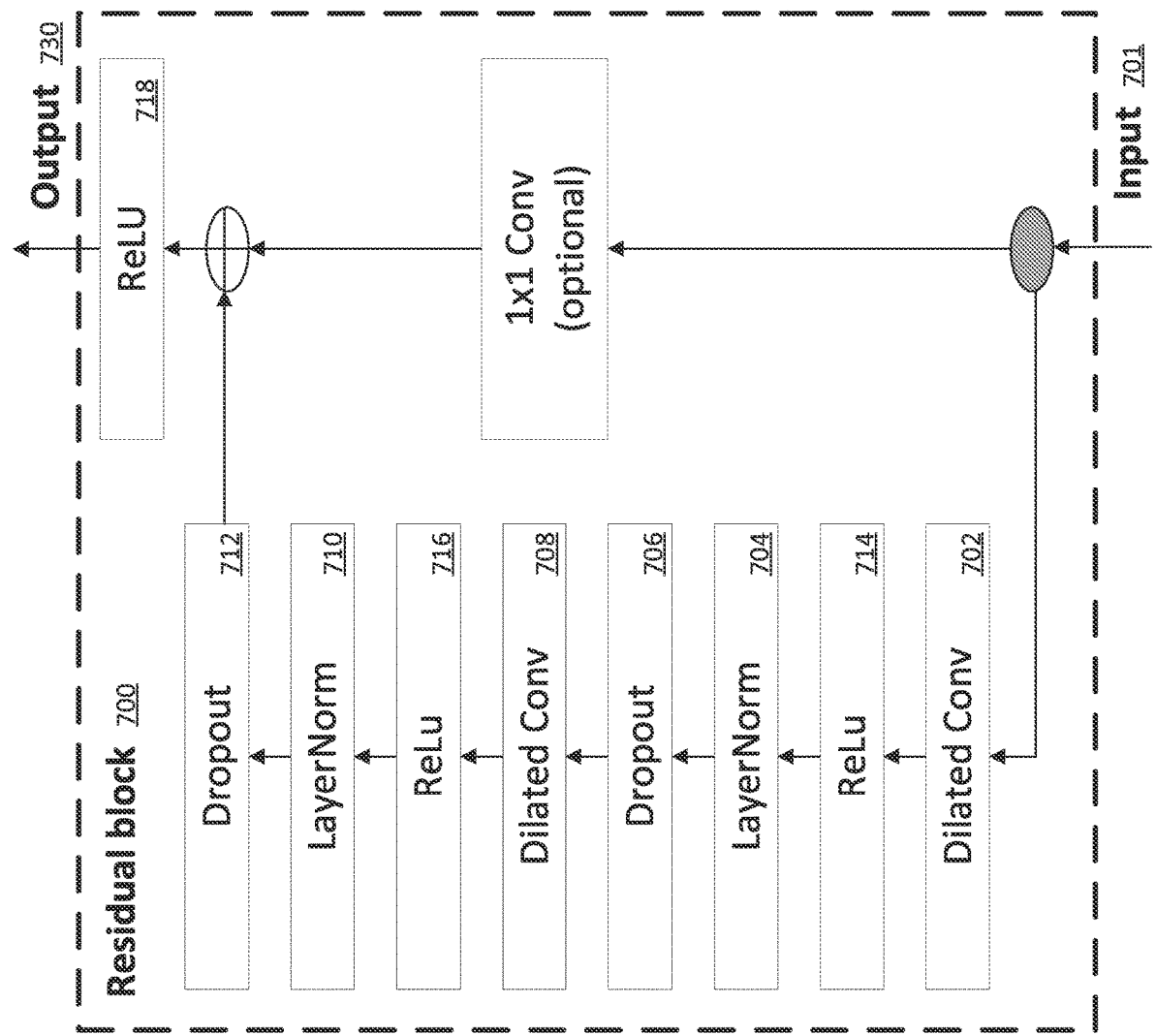
FIG. 7 illustrates a residual block architecture in accordance with an embodiment of the present invention.

FIG. 7 illustrates a residual block architecture in accordance with some embodiments of the present invention.

In some embodiments of the residual block architecture shown in FIG. 7, two one-dimensional (1D) fully dilated convolutional layers 702 and 708 of FIG. 7, are stacked inside a residual block. A layer normalization 704 and 710 in FIG. 7, and a spatial dropout 706 and 712 in FIG. 7, may also be added after each dilated convolution for effective training and regularization in some embodiments of the invention.

Non-linearity such as one or more rectified linear units (ReLUs), shown here as ReLUs 714, 716, and 718 in FIG. 7, may also be included after dilated convolution too. Within a residual block, a skip connection may be used to add the input 701 of the block 700 in FIG. 7 directly into the output 730 of the block, which is useful for deep network training. If the widths of input and output are different, an additional optional 1×1 convolution 720 in FIG. 7 can be applied to the inputs to make it match the width of the output. A plurality of residual blocks may be stacked together as shown in an exemplary manner in FIG. 6 to reach the desired receptive field by increasing dilation factor d exponentially with the depth of the network.

Connectionist Temporal Classification

For tasks like automated speech recognition (ASR), the process is often broken down into a series of subtasks such as speech segmentation, acoustic modelling, and language modelling. Each of these subtasks is then solved by separate, individually trained models. In 2006, Connectionist Temporal Classification (CTC) was introduced by Alex Graves (see Graves, Alex, Supervised Sequence Labeling with Recurrent Neural Networks, volume 385 of Studies in Computational Intelligence, Springer 2012), to allow training deep neural networks end-to-end for tasks such as ASR.

CTC is an objective function that allows a deep learning model to be trained for sequence-to-sequence tasks without requiring any prior alignment between the input and target sequences. More specifically here, CTC is used as a loss function to train the dilated convolutional neural network to minimize the loss between the target sequence of bases and the predicted scan labelling probabilities, which are the output of the network but normalized with the softmax function.

Besides the labels for bases (pure bases with a single nucleotide, A, C, G or T or mixed bases with two nucleotides), an additional 'blank' label is introduced for CTC. There are two important functions of the blank label: First, the blank label can separate bases, especially successive repeat bases such as AAAA. It makes it possible to label the scans which do not belong to any valid bases and to predict the sequence of bases with varying length.

Each input scan can be labelled as bases or blank. A CTC path is a sequence of all scan labels, either bases or blank. The probability of a CTC path is the product of the scan labelling probabilities of all scans in that CTC path. By collapsing the successive repeated labels and then removing the blanks, a CTC path is converted into a basecall sequence. Since many possible CTC paths can be converted into one basecall sequence, the total probability of a basecall sequence is the sum of all probabilities of all possible CTC path for that basecall sequence. For a given input scan sequence x and a target basecall sequence y*, if we write the probability of y* given x as Pr(y*|x), then the CTC loss function is defined as −log(Pr(y*|x)), the negative logarithm of the probability. The dilated convolutional neural network is trained to minimize the CTC loss.

CTC Decoder and Segmentation by Prefix Beam Search

Since many possible CTC paths can be converted into one basecall sequence, the probability of all possible paths yielding the same basecall sequence are calculated and then summed together to give the probability of a basecall sequence. By selecting the basecall sequence with the highest probability, the final basecalling result may be obtained. In embodiments of the present invention discussed herein, CTC Prefix beam search was used to decode CTC output efficiently (See Graves, Alex. Towards End-to-End Speech Recognition with Recurrent Neural Networks, Proceedings of the 31st International Conference on Machine Learning, Beijing, China, 2014. JMLR: W&CP volume 32). In one embodiment of the present invention, a CTC decoder algorithm is employed to decode scan labelling probabilities to generate the final basecall sequence, and then also extend this algorithm to find the scan range and then locate the scan position for each basecalls in the final sequence.

Figure 8:
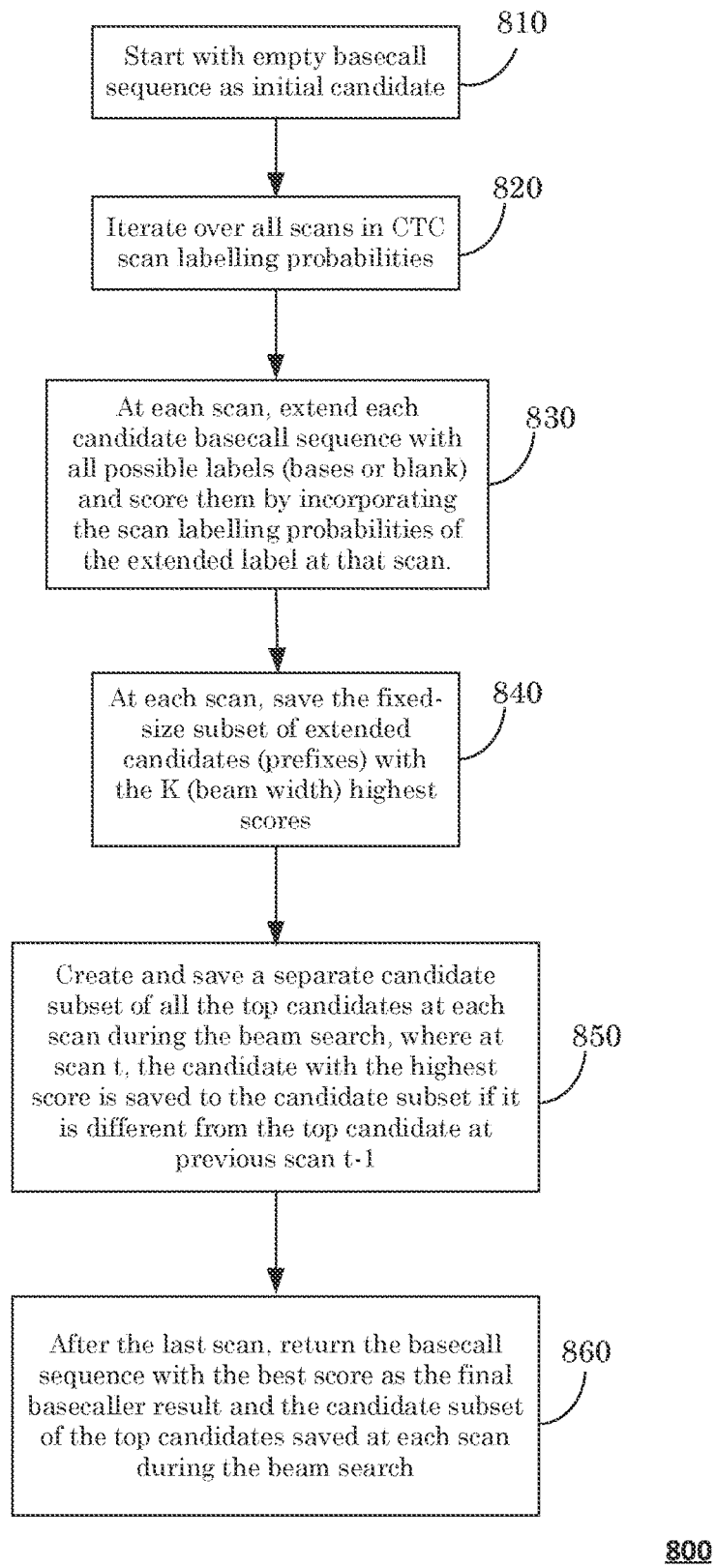
FIG. 8 illustrates a method for generating a basecall sequence in accordance with an embodiment of the present invention.

FIG. 8 illustrates a method 800 for generating a basecall sequence in accordance with an embodiment of the present invention. Prefix beam search starts with the empty basecall sequence as an initial candidate at step 810. Method 800 then iterates over all scans in a window of the input trace to determine CTC scan labelling probabilities in step 820.

In step 830, at each scan in a scan window, all candidate sub-subsequences are extended with all possible labels (all possible options for bases (pure or mixed), or a blank label) and score them by incorporating the scan labelling probabilities of the extended label at that scan. In step 840, the fixed sized subset B of extended candidates with the K highest scores are saved and then extended at the next scan. The candidates at each scan are normally referred to as prefixes and the number of candidates saved, K, is called as beam width. In step 850, a separate candidate subset C is created to save all the top candidates at each scan during beam search. At scan t, the candidate with the highest score is saved to the subset C and the scan t is assigned to this candidate if it is different from the top candidate at previous scan t−1. After the last scan, the basecall sequence with the best score is returned as the final basecaller result, and the candidate subset of the top candidates saved at each scan during beam search is also returned in step 860.

Figure 9:
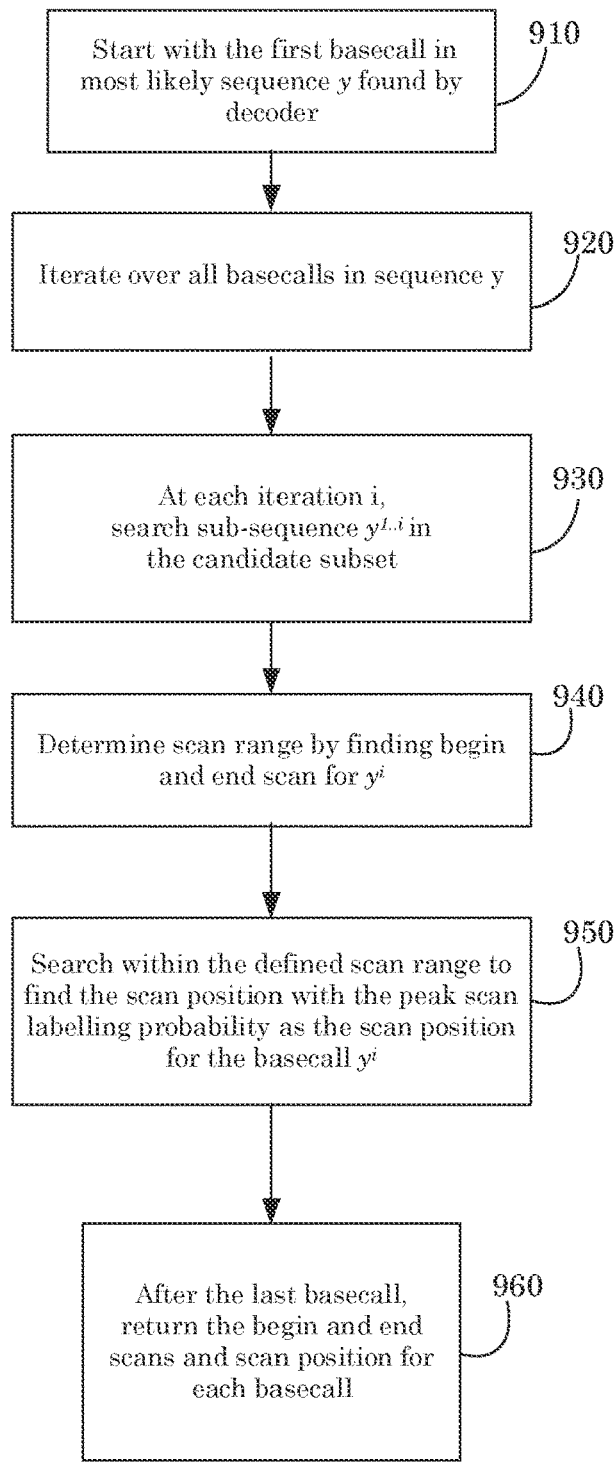
FIG. 9 illustrates a method for generating a scan range and scan position for one or more basecalls in a basecall sequence in accordance with an embodiment of the present invention.

FIG. 9 illustrates a method 900 for generating a scan range and scan position for one or more basecalls in a basecall sequence in accordance with an embodiment of the present invention. In method 900, a basecall sequence y, the most likely sequence found by the decoder in method 800, is denoted as a length L sequence, and the basecall at the position i=1, . . . , L in the sequence is denoted as $y^i$. Method 900 finds the scan position ti for a basecall in position i in sequence y, where i=1, . . . , L.

The method starts at step 910 with the first basecall of the final basecall sequence, where i=1. At iteration i, the sub-sequence $y^{(1 \cdots i)}$ with the first i basecalls in the sequence y is examined at step 920. The method then iterates over all basecalls in the basecall sequence y as shown, by searching the sub-sequence $y^{(1 \cdots i)}$ in the candidate subset C in step 930, until each basecall in the entire basecall sequence y has been examined.

If the examined sub-sequence is in the candidate subset C as determined in method 800, the method 900 continues at step 940, where the scan assigned to the sub-sequence $y^{(1 \cdots i)}$ is used as the begin scan for $y^i$ and then extended by the prefixed scan number nt until the begin scan of next basecall to find the end scan for $y^i$. Once the scan range for $y^i$ is determined, the scan position with the peak scan labelling probability within the defined scan range can be selected as the scan position for the basecall $y^i$ as shown in step 950. At step 960, the scan position and the begin and end scans for each basecall in the entire basecall sequence y is returned.

The pseudocode in Algorithm 1 describes the CTC decoder and segmentation procedure for a CTC network implemented in one embodiment of the present invention. The blank probability, Pb(y,t), is the probability of the output sequence y at a specific time t, originating from one or more CTC paths ending in the blank label. The non-blank probability, Pnb(y,t), is the probability of the output sequence y at a specific time t accounting for all CTC paths ending in a non-blank labels. The total probability, Pt(y,t), is the sum of Pb(y,t) and Pnb(y,t).

Given an input scan sequence x, the probability of emitting the label (or blank) with index k at time t is denoted as Pr(k,t|x). The extension probability Pr(k,y,t) of y by label k at time t is defined as:

$$Pr(k, y, t) = Pr(k, t | x) \begin{cases} Pb(y, t-1) \text{ if } y^e = k \\ Pt(y, t-1) \text{ otherwise} \end{cases}$$

Where $y^e$ is the final label in y. Also define $y^{\leftarrow}$ as the prefix of y with the last label removed, $y^{1, \cdots, i}$ is the sub-sequence of y with the first i labels only, and ∅ as the empty sequence. The algorithm returns the most probable candidate as the final basecall sequence and the begin and end scans, $t_b$ and $t_e$, for each basecall in the final sequence.

---

Algorithm 1 CTC Decoder and Segmentation

---

Initialize: B ← {∅}; Pb(∅, 0) ← 1; Pnb(∅, 0) ← 0; Pt(∅, 0) ← 1
    C ← { }; $\hat{y}_{max}$ ← ∅
for t = 1...T do
  $\hat{B}$ ← the K most probable candidates in B
  B ← { }
  for y ∈ $\hat{B}$ do
    if y ≠ ∅ then
      Pnb(y, t) ← Pnb(y,t − 1)Pr($y^e$, t|x)
      if $\bar{y}$ ∈ $\hat{B}$ then
        Pnb(y, t) ← Pnb(y, t) + Pr($y^e$, $\bar{y}$, t)
    Pb(y,t) ← Pt(y, t − 1)Pr(−, t|x); Pt(y,t) ← Pnb(y,t) + Pb(y,t)
    Add y to B
    for k = 1...K do
      Pb(y + k,t) ← 0
      Pnb(y + k, t) ← Pnb(y + k, t) + Pr(k,y, t)
      Pt(y + k,t) ← Pnb(y + k,t) + Pb(y + k,t)
      Add (y + k) to B
  $y_{max}$ ← $\max_{y \in B}$ Pt(y,t) the most probable candidate in B
  If $y_{max}$ ≠ $\hat{y}_{max}$ then
    $\hat{y}_{max}$ ← $y_{max}$ ; r($y_{max}$) ← t
    Add $y_{max}$ to C
L ← the length of $y_{max}$ ← $\max_{y \in B}$ Pt(y,T)
for i = 1...L do
  if $y_{max}^{1...i}$ ∈ C then
    $t_b$ (i) ← r($y_{max}^{1...i}$)
    if i < L then $t_e$ (i) ← min(r ($y_{max}^{1...i}$) + nt,r($y_{max}^{1...i+1}$) − 1)
    else $t_e$(i) ← min(r ($y_{max}^{1...i}$) + nt, T)
Return: $y_{max}$, $t_b$ and $t_e$

---

Figure 10:
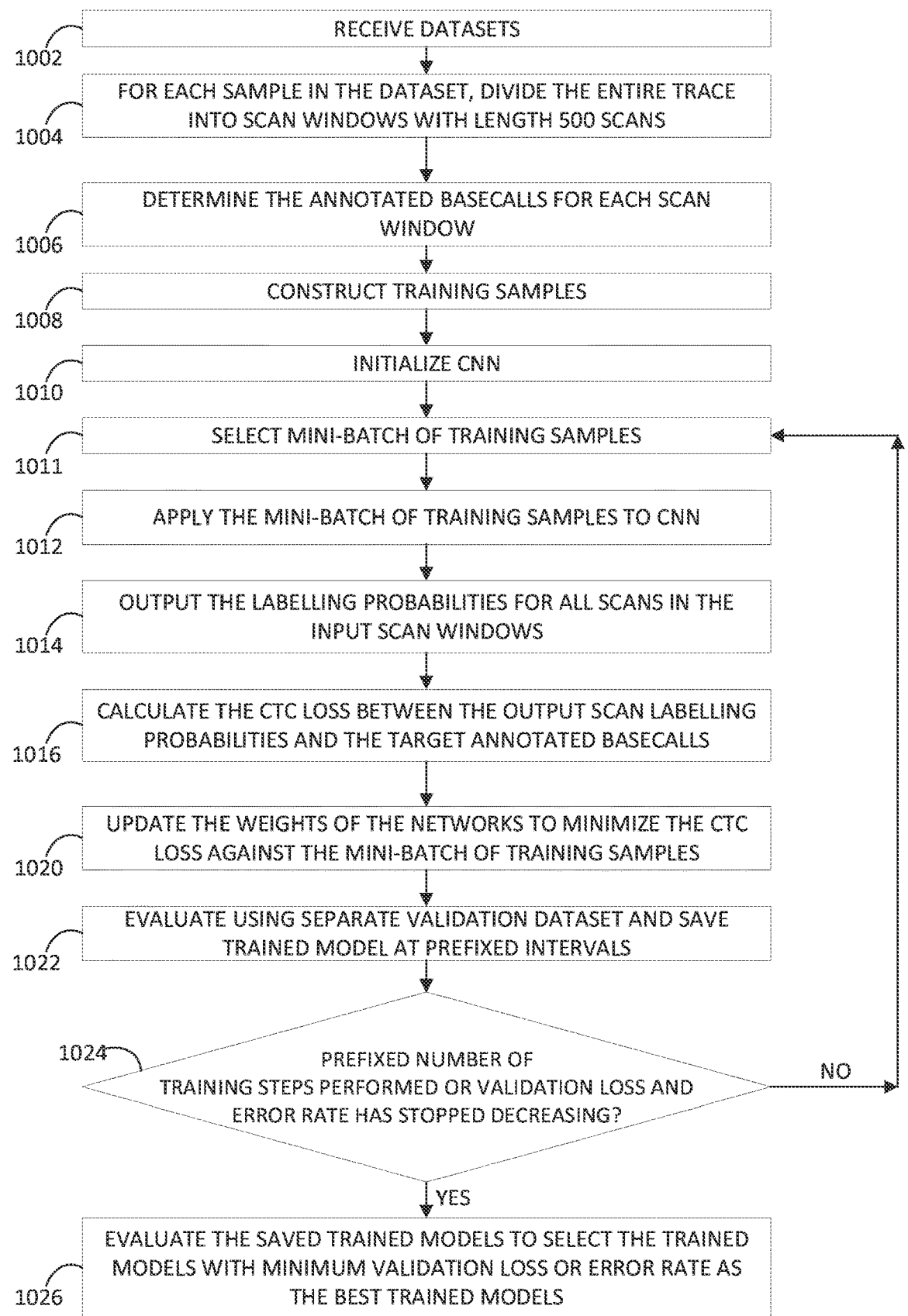
FIG. 10 illustrates a scan labelling model training method in accordance with one embodiment of the present invention.

Referring to FIG. 10, a scan labelling model training method 1000 in one embodiment of the present invention receives sequencing datasets (block 1002). The datasets may include pure base datasets and mixed base datasets. In some embodiments of the invention, the data in these datasets has been annotated and manually reviewed to have the correct basecall sequence ("ground truth") written into each data file (such as a .ab1 data file). In one embodiment, representative data files compiled from data generated using a large variety of CE genetic analyzer and CE DNA analyzer instruments and instrument configurations (e.g., voltage, temperature, chemistry type, capillary array length, etc.) may be used in the sequencing datasets.

For example, in one embodiment of the invention, the pure base dataset may comprise ~49M basecalls and the mixed base dataset may comprise ~13.4M basecalls. The mixed base data set may be composed primarily of pure bases with occasional mixed bases. For each sample in the dataset, the entire trace is divided into scan windows or segments (block 1004). Each scan window may have 500 scan segments. The trace may be a sequence of preprocessed or processed dye RFUs. Additionally, the scan windows for each sample can be shifted by 250 scans to minimize the bias of the scan position on training. The annotated basecalls are listed for each scan window (block 1006). These are utilized as the target sequence during the training. The training samples are then constructed (block 1008). Each of them may comprise the scan window with 500 scans and the respective annotated basecalls. A CNN is initialized (block 1010). In one embodiment of the present invention, the CNN may comprise one or more residual blocks and one 1×1 convolutional reduction layer as shown in FIG. 7. A Softmax layer may be utilized as the output layer of the CNN, which outputs the scan labelling probabilities for all scans in the input trace.

A mini-batch of training samples is then selected (block 1011). The mini-batch may be selected randomly from the training dataset at each training step. The mini-batch of training samples are then applied to the CNN (block 1012). The scan labelling probabilities for all scans in the input scan windows are output (block 1014). The loss between the output scan labelling probabilities and the target annotated basecalls are calculated.

A Connectionist Temporal Classification (CTC) loss function may be utilized to calculate the loss between the output scan labelling probabilities and the target annotated basecalls. The weights of the networks are updated to minimize the CTC loss against the mini-batch of training samples (block 1020). An Adam optimizer or other gradient descent optimizer may be utilized to update the weights. The networks are then saved as a model (block 1022). In some embodiments, the model is saved during specific training steps. The saved model is evaluated utilizing a validation dataset, an independent subset of samples, which are not included in the training process. The scan labelling model training method 1000 then determines whether the validation loss and error rate have stopped decreasing, or a predetermined number of training steps has been reached, whichever comes first (decision block 1024). If not, the scan labelling modelling training method 1000 is re-performed from block 1012 utilizing the network with the updated weights (i.e., the next iteration of the network). Once the validation loss and error rate have stopped decreasing, or a predetermined number of training steps are performed, the saved models are evaluated (block 1026). The best trained models are then selected based on minimum validation loss or error rate from the trained models. These model(s) may then be utilized by the CTC decoder and segmentation basecalling system 540.

In some embodiments, two scan labelling models/neural networks may be generated using scan labelling model training method 1000: one model for a pure base category of data, and a second model for a mixed base category of data.

Embodiments of the present invention can also be trained to call mixed bases, e.g. basecalls of 2, 3, or 4 bases in one position. However, training data from diploid organisms such as human samples, having mixed bases with 2 bases per position, are generally more common than training data from samples with >2 bases per position, such as from some bacterial samples. Mixed basecalling is more challenging than pure basecalling because the peaks of a mixed base position, e.g., two bases in one position, often do not line up exactly superimposed one on the other. Typically, the two peaks may be shifted slightly from each other. Furthermore, in Sanger sequencing, peak heights are often not uniform, and hence the two peaks may be of different peak heights, sometimes even significantly different peak heights.

In some embodiments, data augmentation techniques such as adding noise, spikes, dye blobs or other data artefacts or simulated sequencing trace may be utilized to improve the robustness of the models. Also, during training, other techniques, such as drop-out or weight decay, may be used to improve the generality of the models. Generative Adversarial Nets (GANs) may be utilized to implement these techniques.

Transfer Learning for Customized or Application Specific Models

Transfer Learning has been successfully used to reuse existing neural models for image classification, object recognition, translation, speech synthesis, and many other domains By using transfer learning, the network already trained for general pure or mixed basecalling can be re-trained for customized and application specific models in some embodiments of the present invention. General models learned from existing training datasets may be reused, and just the final 1×1 convolutional reduction layer may be retrained with additional customer or application data to generate specific models for different customers and applications. Since the trained features saved in earlier layers will be reused and only the weights in final layer will be updated, far less customer or application training data is required for training. Transfer learning as used in some embodiments of the present invention may allow customers to leverage their annotated data to optimize the general deep basecalling neural network for better basecalling performance for their specific applications.

Since only the weights of the last 1×1 convolutional reduction layer needed to be re-trained with customer datasets and the number of weights in the last layer ranges from several hundred to several thousand, a customer or application specific dataset of several thousand samples could be enough, which far less than the number of samples used for baseline model training, which can number in the hundreds of thousands.

The process performed by the users to retrain the model is similar. First, select annotated training, validation and test datasets. Then, train the model by using training dataset and monitor the training. Next, select the best trained model by using the validation dataset and test the selected model by the test dataset. However, since the training starts from the general trained model instead of starting from scratch, the number of samples needed are much less and the training time (maybe just a few minutes) is far less compared against the training time needed for baseline model training.

Base Call Quality Values (QV)

The quality value model 560 of FIG. 5 receives the scan labelling probabilities for the assembled scan windows, the basecalls, and the peak scan labelling probability. The quality value model 560 then generates an estimated basecalling error probability. The estimated basecalling error probability may be translated to Phred-style quality scores by the following equation:

$$QV=-10\times\log(\text{Probability of Error}).$$

In another example, Phred (Ewing & Green, 1998) proposed in their Phred Basecaller to use a function of certain parameters computed from the trace data to estimate a probability of error or quality value, negative log-transformed error probability, for each basecall (See Brent Ewing and Phil Green, Base-Calling of Automated Sequencer Traces Using Phred. II. Error Probabilities, Genome Res. 1998 8: 186-194).

Figure 11:
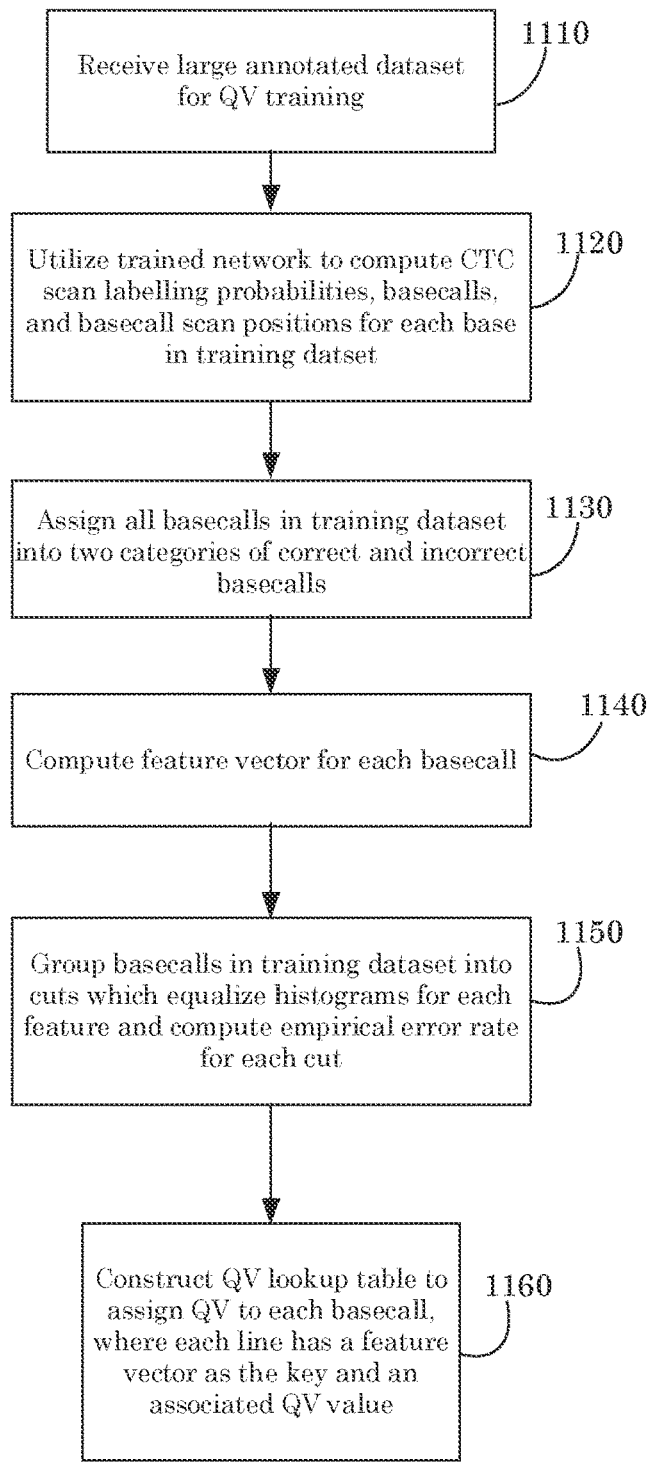
FIG. 11 illustrates a method for constructing a trained quality value lookup table in accordance with one embodiment of the present invention.

A similar strategy has also been applied in genetic sequencing analysis software, such as KB Basecaller manufactured by the Applied Biosystems unit of Thermo Fisher Scientific, Inc. to calculate QV for each basecall (See Labrenz, James, Sorenson, Jon M. and Gehman, Curtis. Methods and systems for the analysis of biological sequence data, WO2004113557A2, 2004 Dec. 29). However, different parameters computed from the trace data are used for QV calculation in KB Basecaller relative to the original Phred basecaller. Similarly, the deep learning basecaller described herein as embodiments of the present invention also calculates quality value to provide an estimation of the confidence of all called bases. Unlike the Phred Basecaller described above and KB Basecaller, the parameters or features used for QV calculation in embodiments of the present invention are based on the CTC scan labelling probabilities instead of trace data. Specifically, a feature vector with four parameters or features listed below are computed from local window of CTC scan labelling probabilities around the basecall scan position for each basecall:

(1) CTC scan labelling probability: CTC scan labelling probability of called base at basecall scan position (2) Noise-to-signal ratio: the ratio of the maximum scan labelling probability from uncalled bases or noise scan labelling probabilities within local windows to the scan labelling probability of called base at basecall scan position (3) Basecall spacing ratio: the ratio of the base spacing between a basecall and their neighboring basecalls (4) Resolution: the ratio of local base spacing to the width of the scan labelling probability peak for the called base FIG. 11 illustrates a method 1100 for constructing a trained quality value lookup table in accordance with one embodiment of the present invention. A large annotated data set is required in QV training to produce one or more QV lookup tables as shown in step 1110.

In one embodiment of the present invention, at step 1120, a convolutional neural network trained using a method as shown in FIG. 6, a decoder using a method as shown in FIG. 8, and a basecall position finder using a method as shown in FIG. 9 are used in to compute CTC scan labelling probabilities, basecalls, and basecall scan positions for each basecall in the training dataset. Whether the basecall in this QV training data set is considered correct or not depends on an alignment between the called and annotated sequences for each sample. All basecalls in the training dataset can be assigned in step 1130 into one of two categories: correct basecalls and incorrect basecalls. A basecall can be characterized by a feature vector, p, with the four features listed above. A feature vector for each basecall is computed in step 1140. All features must be positively and monotonically related to probability of error. In step 1150, the basecalls used for QV training are grouped into many cuts, which equalize histograms for each feature. The empirical error rate is also computed for each cut in step 1150. In step 1160, a lookup table is constructed. The cut with the lowest error rate is added to lookup table first. A new line is added in the lookup table for that cut with a feature vector defining the cut and the QV corresponding to the error rate of that cut ($p_i$, $q_i$). Once a cut is added to lookup table, the calls contained in that cut are also removed from all remaining cuts. This process is repeated until all cuts are added to QV lookup table. The QV lookup table is then complete.

A plurality of trained QV lookup tables can be then used to assign a QV for each basecall. Embodiments of the present invention utilize three separate trained QV tables: one for pure bases in a pure base data category, one for pure bases in a mixed base data category (i.e., a sample that is almost entirely pure bases with occasional mixed bases), and one for mixed bases in a mixed base data category. In some embodiments of the present invention, the QV lookup table training may be done twice: once using the pure base dataset to create the pure base data category QV table, and a second time using the mixed base dataset to create the pure base in a mixed base data category QV table, as well as the mixed base in a mixed base category QV table.

For a called base, the feature vector, p, for that basecall is calculated. The feature vector is then used as a query key to search the lookup table line by line, in order, until a line with all feature values larger or equal to the corresponding features for that basecall. The QV associated to that line is then assigned to that basecall. The basecalls with no lines found are assigned to QV=0.

Exemplary Computing Device Embodiment

Figure 12:
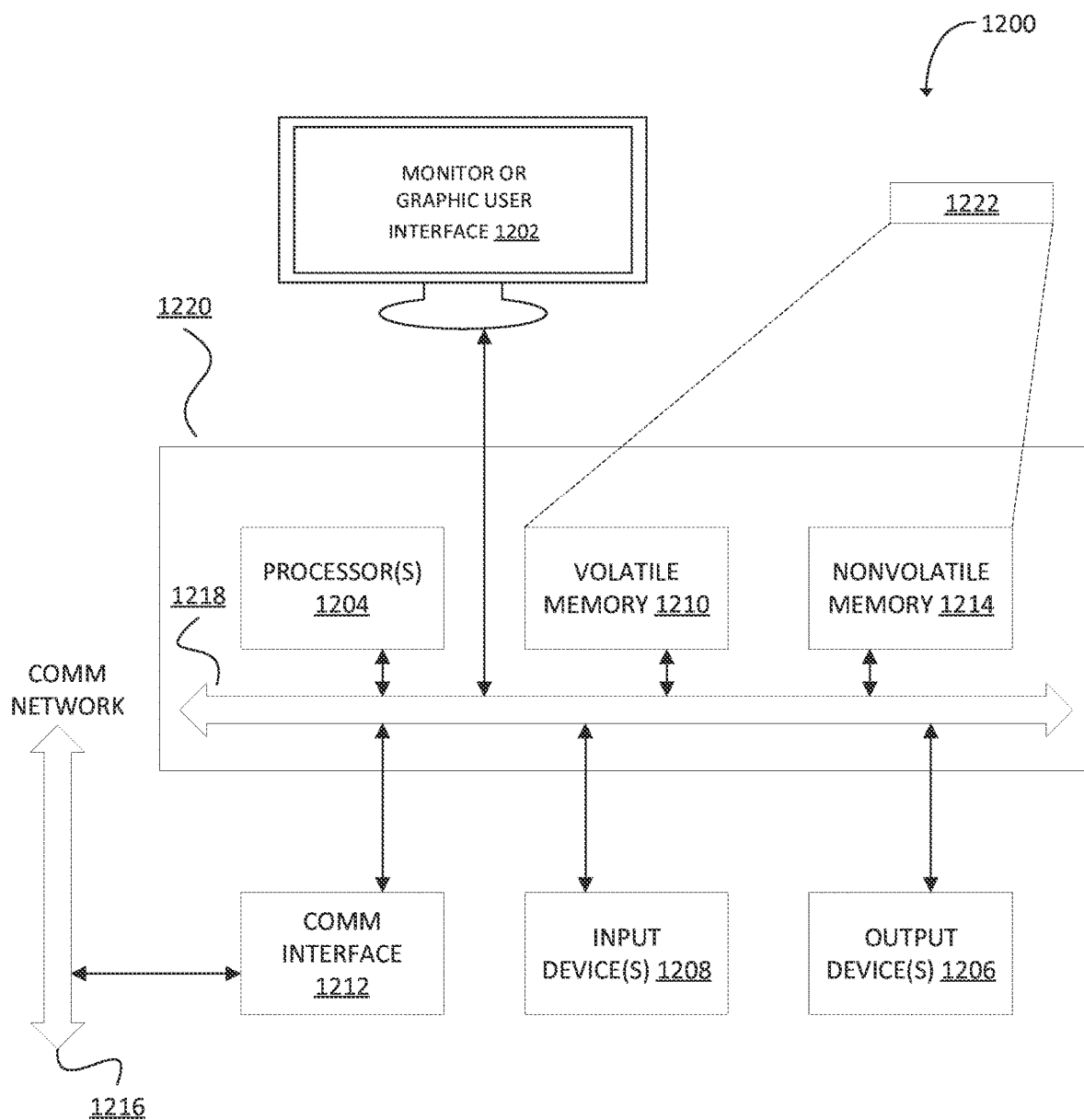
FIG. 12 illustrates a block diagram of an exemplary computing device that may incorporate embodiments of the present invention.

FIG. 12 is an example block diagram of a computing device 1200 that may incorporate embodiments of the present invention. FIG. 12 is merely illustrative of a machine system to carry out aspects of the technical processes described herein, and does not limit the scope of the claims One of ordinary skill in the art would recognize other variations, modifications, and alternatives. In one embodiment, the computing device 1200 typically includes a monitor or graphical user interface 1202, a data processing system 1220, a communication network interface 1212, input device(s) 1208, output device(s) 1206, and the like.

As depicted in FIG. 12, the data processing system 1220 may include one or more processor(s) 1204 that communicate with a number of peripheral devices via a bus subsystem 1218. These peripheral devices may include input device(s) 1208, output device(s) 1206, communication network interface 1212, and a storage subsystem, such as a volatile memory 1210 and a nonvolatile memory 1214. The volatile memory 1210 and/or the nonvolatile memory 1214 may store computer-executable instructions and thus forming logic 1222 that when applied to and executed by the processor(s) 1204 implement embodiments of the processes disclosed herein.

The input device(s) 1208 include devices and mechanisms for inputting information to the data processing system 1220. These may include a keyboard, a keypad, a touch screen incorporated into the monitor or graphical user interface 1202, audio input devices such as voice recognition systems, microphones, and other types of input devices. In various embodiments, the input device(s) 1208 may be embodied as a computer mouse, a trackball, a track pad, a joystick, wireless remote, drawing tablet, voice command system, eye tracking system, and the like. The input device(s) 1208 typically allow a user to select objects, icons, control areas, text and the like that appear on the monitor or graphical user interface 1202 via a command such as a click of a button or the like.

The output device(s) 1206 include devices and mechanisms for outputting information from the data processing system 1220. These may include the monitor or graphical user interface 1202, speakers, printers, infrared LEDs, and so on as well understood in the art.

The communication network interface 1212 provides an interface to communication networks (e.g., communication network 1216) and devices external to the data processing system 1220. The communication network interface 1212 may serve as an interface for receiving data from and transmitting data to other systems. Embodiments of the communication network interface 1212 may include an Ethernet interface, a modem (telephone, satellite, cable, ISDN), (asynchronous) digital subscriber line (DSL), FireWire, USB, a wireless communication interface such as Bluetooth or WiFi, a near field communication wireless interface, a cellular interface, and the like. The communication network interface 1212 may be coupled to the communication network 1216 via an antenna, a cable, or the like. In some embodiments, the communication network interface 1212 may be physically integrated on a circuit board of the data processing system 1220, or in some cases may be implemented in software or firmware, such as "soft modems", or the like. The computing device 1200 may include logic that enables communications over a network using protocols such as HTTP, TCP/IP, RTP/RTSP, IPX, UDP and the like.

The volatile memory 1210 and the nonvolatile memory 1214 are examples of tangible media configured to store computer readable data and instructions forming logic to implement aspects of the processes described herein. Other types of tangible media include removable memory (e.g., pluggable USB memory devices, mobile device SIM cards), optical storage media such as CD-ROMS, DVDs, semiconductor memories such as flash memories, non-transitory read-only-memories (ROMS), battery-backed volatile memories, networked storage devices, and the like. The volatile memory 1210 and the nonvolatile memory 1214 may be configured to store the basic programming and data constructs that provide the functionality of the disclosed processes and other embodiments thereof that fall within the scope of the present invention. Logic 1222 that implements embodiments of the present invention may be formed by the volatile memory 1210 and/or the nonvolatile memory 1214 storing computer readable instructions. Said instructions may be read from the volatile memory 1210 and/or nonvolatile memory 1214 and executed by the processor(s) 1204. The volatile memory 1210 and the nonvolatile memory 1214 may also provide a repository for storing data used by the logic 1222. The volatile memory 1210 and the nonvolatile memory 1214 may include a number of memories including a main random access memory (RAM) for storage of instructions and data during program execution and a read only memory (ROM) in which read-only non-transitory instructions are stored. The volatile memory 1210 and the nonvolatile memory 1214 may include a file storage subsystem providing persistent (non-volatile) storage for program and data files. The volatile memory 1210 and the nonvolatile memory 1214 may include removable storage systems, such as removable flash memory.

The bus subsystem 1218 provides a mechanism for enabling the various components and subsystems of data processing system 1220 communicate with each other as intended. Although the communication network interface 1212 is depicted schematically as a single bus, some embodiments of the bus subsystem 1218 may utilize multiple distinct busses.

It will be readily apparent to one of ordinary skill in the art that the computing device 1200 may be a device such as a smartphone, a desktop computer, a laptop computer, a rack-mounted computer system, a computer server, or a tablet computer device. As commonly known in the art, the computing device 1200 may be implemented as a collection of multiple networked computing devices. Further, the computing device 1200 will typically include operating system logic (not illustrated) the types and nature of which are well known in the art.

One embodiment of the present invention includes systems, methods, and a non-transitory computer readable storage medium or media tangibly storing computer program logic capable of being executed by a computer processor.

Those skilled in the art will appreciate that computer system 1200 illustrates just one example of a system in which a computer program product in accordance with an embodiment of the present invention may be implemented. To cite but one example of an alternative embodiment, execution of instructions contained in a computer program product in accordance with an embodiment of the present invention may be distributed over multiple computers, such as, for example, over the computers of a distributed computing network.

While the present invention has been particularly described with respect to the illustrated embodiments, it will be appreciated that various alterations, modifications and adaptations may be made based on the present disclosure and are intended to be within the scope of the present invention. While the invention has been described in connection with what are presently considered to be the most practical and preferred embodiments, it is to be understood that the present invention is not limited to the disclosed embodiments but, on the contrary, is intended to cover various modifications and equivalent arrangements included within the scope of the underlying principles of the invention as described by the various embodiments referenced above and below.

Terminology

Terminology used herein with reference to embodiments of the present invention disclosed in this document should be accorded its ordinary meaning according to those of ordinary skill in the art unless otherwise indicated expressly or by context.

"Quality values" in this context refers to an estimate (or prediction) of the likelihood that a given basecall is in error. Typically, the quality value is scaled following the convention established by the Phred program: QV=−10 log 10(Pe), where Pe stands for the estimated probability that the call is in error. See Brent Ewing and Phil Green, Base-Calling of Automated Sequencer Traces Using Phred. II. Error Probabilities, Genome Res. 1998 8: 186-194. Quality values are a measure of the certainty of the basecalling and consensus-calling algorithms. Higher values correspond to lower chance of algorithm error. Sample quality values refer to the per base quality values for a sample, and consensus quality values are per-consensus quality values.

"Sigmoid function" in this context refers to a function of the form $f(x)=1/(exp(-x))$. The sigmoid function is used as an activation function in artificial neural networks. It has the property of mapping a wide range of input values to the range 0-1, or sometimes −1 to 1.

"Capillary electrophoresis genetic analyzer" or "capillary electrophoresis DNA analyzer" in this context refers to instrument that applies an electrical field to a capillary loaded with a biological sample so that the negatively charged DNA fragments move toward the positive electrode. The speed at which a DNA fragment moves through the medium is inversely proportional to its molecular weight. This process of electrophoresis can separate the extension products by size at a resolution of one base.

"Image signal" in this context refers to an intensity reading of fluorescence from one of the dyes used to identify bases during a data run. In one embodiment of the present invention, signal strength numbers are shown in an Annotation view of the sample file.

"Exemplary commercial CE devices" in this context may refer to and include, but are not limited to, the following: the Applied Biosystems, Inc. (ABI) genetic analyzer models 310 (single capillary), 3130 (4 capillary), 3130xL (16 capillary), 3500 (8 capillary), 3500xL (24 capillary), and the SeqStudio genetic analyzer models; DNA analyzer models 3730 (48 capillary), and 3730xL (96 capillary); as well as the Agilent 7100 device, Prince Technologies, Inc.'s PrinCE™ Capillary Electrophoresis System, Lumex, Inc.'s Capel-105™ CE system, and Beckman Coulter's P/ACE™ MDQ systems, among others.

"Base pair" in this context refers to complementary nucleotides in a DNA sequence. Thymine (T) is complementary to adenine (A) and guanine (G) is complementary to cytosine (C).

"ReLU" in this context refers to a rectified linear activation function unit, a piecewise linear function that will output the input directly if it is positive; otherwise, it will output zero. It is also known as a ramp function and is analogous to half-wave rectification in electrical signal theory. ReLU is a popular activation function in deep neural networks.

"Heterozygous insertion deletion variant" (or "het indel") in this context refers to a polymorphism in which one copy of a DNA sequence has an insertion or deletion relative to the other copy being sequenced together simultaneously. The result of sequencing a het indel is that downstream of the heterozygous insertion or deletion there are two peaks (also known as mixed bases) at the majority of positions.

"Mobility shift" in this context refers to electrophoretic mobility differences imposed by the presence of different fluorescent dye molecules associated with differently labeled reaction extension products.

"Variant" in this context refers to bases where the consensus sequence differs from the reference sequence that is provided.

"Polymerase slippage" in this context results in the presence of minor peaks 3' to a homopolymer. The polymerase can "slip" when sequencing a long homopolymer stretch, skipping one or more bases within the homopolymer, thereby creating shortened products that differ in length by one to a few bases that appear as minor peaks within and downstream of the homopolymer.

"Amplicon" in this context refers to the product of a PCR reaction. Typically, an amplicon is a short piece of DNA.

"Basecall" in this context refers to assigning a nucleotide base to each peak (IUPAC-IUB notation: A, C, G, T) of the fluorescent signal. Basecalls can also be mixed, with 2 peaks in one position (IUPAC-IUB notation: R=A and G, Y=C and T, S=G and C, W=A and T, K=G and T, and M=A and C), or 3 peaks in one position (IUPAC-IUB notation: B=C and G and T, D=A and G and T, H=A and C and T, V=A and C and G).

"Raw data" or "input analyzed trace" in this context refers to a multicolor graph displaying the fluorescence intensity (signal) collected for each of the four fluorescent dyes, and/or data that is used to populate or create such a graph.

"Base spacing" in this context refers to the number of data points from one peak to the next. A negative spacing value or a spacing value shown in red indicates that the basecaller used a default spacing value rather than one calculated based on the current data.

"Separation or sieving media" in this context refers to non-gel liquid polymers such as linear polyacrylamide, hydroxyalkyl cellulose (HEC), agarose, and cellulose acetate, and the like can be used. Other separation media that can be used for capillary electrophoresis include, but are not limited to, water soluble polymers such as poly(N,N'-dimethyl acrylamide)(PDMA), polyethylene glycol (PEG), poly (vinylpyrrolidone) (PVP), polyethylene oxide, polysaccharides and pluronic polyols; various polyvinyl alcohol (PVAL)-related polymers, polyether-water mixture, lyotropic polymer liquid crystals, among others.

"Adam optimizer" in this context refers to an optimization algorithm that can be used instead of the classical stochastic gradient descent procedure to update network weights iteratively based on training data. Stochastic gradient descent maintains a single learning rate (termed alpha) for all weight updates and the learning rate does not change during training. A learning rate is maintained for each network weight (parameter) and separately adapted as learning unfolds. Adam optimizers combine the advantages of two other extensions of stochastic gradient descent: specifically, Adaptive Gradient Algorithm (AdaGrad) that maintains a per-parameter learning rate that improves performance on problems with sparse gradients (e.g. natural language and computer vision problems), and Root Mean Square Propagation (RMSProp) that also maintains per-parameter learning rates that are adapted based on the average of recent magnitudes of the gradients for the weight (e.g. how quickly it is changing). This means the algorithm does well on online and non-stationary problems. Adam realizes the benefits of both AdaGrad and RMSProp. Instead of adapting the parameter learning rates based on the average of the first moments (the means) as in RMSProp, Adam also makes use of the average of the second moments of the gradients (the uncentered variances). Specifically, the algorithm calculates an exponential moving average of the gradient and the squared gradient, and the parameters beta1 and beta2 control the decay rates of these moving averages. The initial value of the moving averages and beta1 and beta2 values close to 1.0 (recommended) result in a bias of moment estimates towards zero. This bias is overcome by first calculating the biased estimates before then calculating bias-corrected estimates.

"Hyperbolic tangent function" in this context refers to a function of the form tanh(x)=sin h(x)/cos h(x). The tanh function is a popular activation function in artificial neural networks. Like the sigmoid, the tanh function is also sigmoidal ("s"-shaped), but instead outputs values that range (−1, 1). Thus, strongly negative inputs to the tanh will map to negative outputs. Additionally, only zero-valued inputs are mapped to near-zero outputs. These properties make the network less likely to get "stuck" during training.

"Relative fluorescence unit" in this context refers to measurements in electrophoresis methods, such as capillary electrophoresis methods for DNA sequencing analysis. A "relative fluorescence unit" is a unit of measurement used in analysis which employs fluorescence detection.

"CTC loss function" in this context refers to connectionist temporal classification, a type of neural network output and associated scoring function, for training recurrent neural networks (RNNs) such as LSTM networks, temporal convolutional networks (TCNs), or dilated causal or non-causal convolution networks to tackle sequence problems where the timing is variable. A CTC network has a continuous output (e.g. Softmax), which is fitted through training to model the probability of a label. CTC does not attempt to learn boundaries and timings: Label sequences are considered equivalent if they differ only in alignment, ignoring blanks Equivalent label sequences can occur in many ways—which makes scoring a non-trivial task. Fortunately, scoring of equivalent label sequences may be completed using the Forward-Backward algorithm. CTC scores can then be used with the back-propagation algorithm to update the neural network weights. Alternative approaches to a CTC-fitted neural network include a hidden Markov model (HMM).

"Polymerase" in this context refers to an enzyme that catalyzes polymerization. DNA and RNA polymerases build single-stranded DNA or RNA (respectively) from free nucleotides, using another single-stranded DNA or RNA as the template.

"Sample data" in this context refers to the output of a single lane or capillary on a sequencing instrument. Sample data can be entered into Sequencing Analysis, SeqScape, and other sequencing analysis software manufactured by Applied Biosystems, Inc. and other manufacturers.

"Plasmid" in this context refers to a genetic structure in a cell that can replicate independently of the chromosomes, typically a small circular DNA molecule in the cytoplasm of a bacterium or protozoan. Plasmids are often used in the laboratory manipulation of genes.

"Beam search" in this context refers to a heuristic search algorithm that explores a graph by expanding the most promising node in a limited set. Beam search is an optimization of best-first search that reduces its memory requirements. Best-first search is a graph search which orders all partial solutions (states) according to some heuristic. But in beam search, only a predetermined number of best partial solutions are kept as candidates. It is thus a greedy algorithm. Beam search uses breadth-first search to build its search tree. At each level of the tree, it generates all successors of the states at the current level, sorting them in increasing order of heuristic cost. However, it only stores a predetermined number, K, of best states at each level (called the beam width). Only those states are expanded next. The greater the beam width, the fewer states are pruned. With an infinite beam width, no states are pruned and beam search is identical to breadth-first search. The beam width bounds the memory required to perform the search. Since a goal state could potentially be pruned, beam search sacrifices completeness (the guarantee that an algorithm will terminate with a solution, if one exists). Beam search is not optimal (that is, there is no guarantee that it will find the best solution). In general, beam search returns the first solution found. Beam search for machine translation is a different case: once reaching the configured maximum search depth (i.e. translation length), the algorithm will evaluate the solutions found during search at various depths and return the best one (the one with the highest probability). The beam width can either be fixed or variable. One approach that uses a variable beam width starts with the width at a minimum. If no solution is found, the beam is widened and the procedure is repeated.

"Sanger Sequencing" in this context refers to a DNA sequencing process that takes advantage of the ability of DNA polymerase to incorporate 2',3'-dideoxynucleotides—nucleotide base analogs that lack the 3'-hydroxyl group essential in phosphodiester bond formation. As originally designed, Sanger dideoxy sequencing required a DNA template, a sequencing primer, DNA polymerase, deoxynucleotides (dNTPs), dideoxynucleotides (ddNTPs), and reaction buffer. Four separate reactions are set up, each containing radioactively labeled nucleotides and either ddA, ddC, ddG, or ddT. The annealing, labeling, and termination steps are performed on separate heat blocks. DNA synthesis is performed at 37° C., the temperature at which DNA polymerase has the optimal enzyme activity. DNA polymerase adds a deoxynucleotide or the corresponding 2',3'-dideoxynucleotide at each step of chain extension. Whether a deoxynucleotide or a dideoxynucleotide is added depends on the relative concentration of both molecules. When a deoxynucleotide (A, C, G, or T) is added to the 3' end, chain extension can continue. However, when a dideoxynucleotide (ddA, ddC, ddG, or ddT) is added to the 3' end, chain extension terminates. Sanger dideoxy sequencing results in the formation of extension products of various lengths terminated with dideoxynucleotides at the 3' end.

"Single nucleotide polymorphism" in this context refers to a variation in a single base pair in a DNA sequence.

"Mixed base" in this context refers to one-base positions that contain 2, 3, or 4 bases. These bases are assigned the appropriate IUB code.

"Softmax function" in this context refers to a function of the form f(xi)=exp(xi)/sum(exp(x)) where the sum is taken over a set of x. Softmax is used at different layers (often at the output layer) of artificial neural networks to predict classifications for inputs to those layers. The Softmax function calculates the probabilities distribution of the event xi over 'n' different events. In general sense, this function calculates the probabilities of each target class over all possible target classes. The calculated probabilities are helpful for predicting that the target class is represented in the inputs. The main advantage of using Softmax is the output probabilities range. The range will be from 0 to 1, and the sum of all the probabilities will be equal to one. If the softmax function used for multi-classification model it returns the probabilities of each class and the target class will have the high probability. The formula computes the exponential (e-power) of the given input value and the sum of exponential values of all the values in the inputs. Then the ratio of the exponential of the input value and the sum of exponential values is the output of the softmax function.

"Noise" in this context refers to average background fluorescent intensity for each dye.

"Backpropagation" in this context refers to an algorithm used in artificial neural networks to calculate a gradient that is needed in the calculation of the weights to be used in the network. It is commonly used to train deep neural networks, a term referring to neural networks with more than one hidden layer. For backpropagation, the loss function calculates the difference between the network output and its expected output, after a case propagates through the network.

"Dequeue max finder" in this context refers to an algorithm utilizing a double-ended queue to determine a maximum value.

"Pure base" in this context refers to one-base positions that contain only one base or nucleotide (A, C, G, and T). These bases are assigned the appropriate IUPAC-IUB code.

"Primer" in this context refers to a short single strand of DNA that serves as the priming site for DNA polymerase in a PCR reaction.

"Loss function" (sometime referred to as a cost function or error function) in this context refers to, is a function that maps values of one or more variables onto a real number intuitively representing some "cost" associated with those values.

What is claimed is:

1. A method of automatically sequencing one or more deoxyribonucleic acid (DNA) molecules of a biological sample, comprising:
   a. using a capillary electrophoresis (CE) genetic analyzer to measure the biological sample to obtain an input trace comprising digital data corresponding to fluorescent values comprising a plurality of scans of the biological sample;
   b. using a trained artificial neural network comprising a plurality of layers including convolutional layers to generate scan labelling probabilities for the plurality of scans; and
   c. determining a basecall sequence comprising a plurality of basecalls for the one or more DNA molecules based on the scan labelling probabilities for each of the plurality of scans,
   wherein the plurality of layers comprises a plurality of residual blocks,
   wherein each residual block of the plurality of residual blocks comprises
   one or more non-causal convolutional layers.

2. The method of claim 1, further comprising:
   a. determining a scan number position for each of the plurality of basecalls;
   b. displaying, on an electronic display, the basecall sequence; and
   c. using the scan number position to display, on the electronic display, a basecall position indication for each of the plurality of basecalls that visually indicates a relative spacing between adjacent basecalls in the basecall sequence.

3. The method of claim 2, further comprising displaying, on the electronic display, the input trace such that an axis of the input trace corresponding to relative scan number positions of fluorescent values of the input trace is aligned with an axis for displaying the basecall position indications corresponding to relative scan number positions.

4. The method of claim 3 wherein the axis of the input trace is the same axis as the axis for displaying the basecall position indications.

5. The method of claim 2 further comprising displaying, on the electronic display, a visual indication of a quality value for each of the plurality of basecalls.

6. The method of claim 2 further comprising displaying a visual indication of a quality value for each of the plurality of basecalls wherein the visual indication of the quality value is also used as the basecall position indication by placing the visual indication of the quality value at a location on the electronic display that represents the basecall position.

7. The method of claim 1, wherein a residual block of the plurality of residual blocks further comprises a skip connection.

8. The method of claim 7, wherein a residual block of the plurality of residual blocks further comprises a 1×1 convolutional layer between an input and an output of the skip connection.

9. The method of claim 1, wherein a residual block of the plurality of residual blocks further comprises at least one spatial dropout layer following a non-causal convolution layer.

10. The method of claim 1, wherein a residual block of the plurality of residual blocks further comprises at least one normalization layer following a non-causal convolution layer.

11. The method of claim 1, wherein a residual block of the plurality of residual blocks further comprises at least one rectified linear activation function layer following a non-causal convolution layer.

12. The method of claim 1, wherein the plurality of residual blocks comprises at least a first residual block comprising one or more non-causal convolutional layers having a first dilation factor, and a second residual block comprising one or more non-causal convolutional layers having a second dilation factor different than the first dilation factor.

13. The method of claim 1, wherein the trained artificial neural network has been trained using a Connectionist Temporal Classification (CTC) loss function to minimize a loss between the scan labelling probabilities and a target sequence of bases.

14. The method of claim 1, wherein the trained artificial neural network further comprises a 1×1 convolutional reduction layer to reduce a number of extracted features to match a number of output labels.

15. The method of claim 1, wherein the trained artificial neural network further comprises a softmax layer to obtain the scan labelling probabilities.

16. The method of claim 1, wherein determining the basecall sequence further comprises decoding the scan labelling probabilities using a prefix beam search.

17. The method of claim 16, wherein decoding the scan labelling probabilities using the prefix beam search comprises:
   a. initializing an empty basecall sequence as a prefix;
   b. at each scant of the plurality of scans,
      i. extending the prefixes with each of a plurality of extended labels;
      ii. scoring each prefix by incorporating a scan labelling probability of the extended label at the scan t;
      iii. saving an extended candidate subset comprising the K highest scoring prefixes wherein the subset does not exceed a beam width of size K;
      iv. saving the highest scoring prefix at the scan in a candidate subset if the prefix is different from the highest scoring prefix at the previous scan t−1;
      v. assigning the scan to the highest scoring prefix if the prefix is different from the highest scoring prefix at the previous scan t−1;
      vi. returning the highest scoring prefix at the last scan as the final basecall sequence; and
      vii. returning the candidate subset of the top candidates saved at each scan during the prefix beam search.

18. The method of claim 17, wherein the plurality of extended labels comprises pure base labels, mixed base labels, and a blank label.

19. The method of claim 17, further comprising finding a scan range for each basecall and then using the scan range to find a scan position having a peak labelling probability within the scan range.

20. The method of claim 19, wherein finding the scan range and the scan position with the peak labelling probability within the scan range for each basecall comprises:
   a. starting with a first basecall in a final basecall sequence y;
   b. at each basecall $y^i$ of the plurality of basecalls in the final basecall sequence y,
      i. searching the basecall sub-sequence $y^1 \cdots ^i$, with the first i basecalls in the basecall sequence y in the candidate subset;
      ii. setting a begin scan of the scan range for the basecall $y^i$ as the scan assigned to the found candidate;
      iii. setting an end scan of the scan range for the basecall $y^i$ by extending the begin scan with the prefixed scan number until the start scan of a next basecall $y^{i+1}$; and
      iv. selecting a scan position for the basecall $y^i$, between the begin scan and the end scan with the peak labelling probability; and
   c. returning the begin and end scans and the scan positions for all basecalls in the final basecall sequence.

21. The method of claim 1, further comprising determining a quality value for each of the plurality of basecalls by, for a basecall of the plurality of basecalls, using a plurality of feature values derived from scan labelling probabilities corresponding to scans in scan range that includes a scan position of the basecall, the plurality of feature values comprising a peak scan labelling probability of the basecall, a noise-to-signal ratio, a basecall spacing ratio, and a resolution value.

22. The method of claim 21, further comprising using a machine learning algorithm to obtain the quality value using the plurality of feature values.

23. The method of claim 21, wherein the noise-to-signal ratio comprises a ratio of (1) a maximum scan labelling probability from one or more uncalled bases or noise scan labelling probabilities within the local scan window for the basecall, to (2) the scan labelling probability of the called base at a scan position for the basecall.

24. The method of claim 21, wherein the basecall spacing ratio comprises a ratio of a first base spacing value between the basecall and a first neighboring basecall and a second base spacing value between the basecall and a second neighboring basecall.

25. The method of claim 21, wherein the resolution value comprises a ratio of a local base spacing value to a width value of a scan labelling probability peak for the basecall.

26. The method of claim 1, further comprising determining a quality value for each basecall, wherein determining the quality value comprises:
   a. determining a feature vector for the basecall, the feature vector comprising a plurality of feature values including: a scan labelling probability of the basecall at a basecall scan position, a noise-to-signal ratio, a basecall spacing ratio, and a resolution value;
   b. finding a line having a smallest cut index in a quality value lookup table comprising a plurality of lines wherein each line has (1) a feature vector assigned to a cut comprising a plurality of basecalls, and (2) a quality value corresponding to an empirical error rate of the cut; and
   c. traversing the quality value lookup table in order to assign a quality value corresponding to the line having the smallest cut index to the basecall, where the line having the smallest cut index comprises the line having a feature vector having all feature values greater than or equal to the feature vector for the basecall, or assigning a quality value of zero if no line having the smallest cut index is found.

27. The method of claim 26, wherein the quality value lookup table is constructed by:
   a. initializing a quality value lookup table;
   b. computing a feature vector for each basecall in a quality value training dataset comprising a plurality of samples;
   c. until all remaining cuts are added to the lookup table, grouping the basecalls into a plurality of cuts wherein each cut equalizes a histogram for the feature vector;
   d. computing an empirical error rate for each of the one or more cuts;
   e. adding a cut having the lowest empirical error rate to the quality value lookup table as a next new line comprising a feature vector assigned to the cut and a quality value corresponding to the empirical error rate of the cut;
   f. removing the cut added to the quality value lookup table from the plurality of cuts;
   g. removing all basecalls in the cut added to the quality value lookup table from the remaining cuts; and
   h. repeating steps (c) through (g) until there are no more cuts remaining.

28. The method of claim 1, further comprising displaying the basecall sequence and the input analyzed trace in an electropherogram on a computing device display.

29. A non-transitory computer readable medium comprising a memory storing one or more instructions which, when executed by a one or more processors of at least one computing device, perform automatically sequencing one or more deoxyribonucleic acid (DNA) molecules of a biological sample by:
 a. obtaining an input trace comprising digital data corresponding to fluorescent values in a plurality of scans of the biological sample conducted by a capillary electrophoresis genetic analyzer;
 b. using a trained artificial neural network comprising a plurality of layers including convolutional layers to generate scan labelling probabilities for the plurality of scans; and
 c. determining a basecall sequence comprising a plurality of basecalls for the one or more DNA molecules based on the scan labelling probabilities for each of the plurality of scans,
 wherein the plurality of layers comprises a plurality of residual blocks, wherein each residual block of the plurality of residual blocks comprises one or more non-causal convolutional layers.

30. A method of automatically sequencing one or more deoxyribonucleic acid (DNA) molecules of a biological sample, comprising:
 a. using a capillary electrophoresis (CE) genetic analyzer to measure the biological sample to obtain an input trace comprising digital data corresponding to fluorescent values comprising a plurality of scans of the biological sample;
 b. using a trained artificial neural network comprising a plurality of layers including convolutional layers to generate scan labelling probabilities for the plurality of scans; and
 c. determining a basecall sequence comprising a plurality of basecalls for the one or more DNA molecules based on the scan labelling probabilities for each of the plurality of scans;
 d. determining a scan number position for each of the plurality of basecalls;
 e. displaying, on an electronic display, the basecall sequence; and
 f. using the scan number position to display, on the electronic display, a basecall position indication for each of the plurality of basecalls that visually indicates a relative spacing between adjacent basecalls in the basecall sequence.

31. The method of claim 30, further comprising displaying, on the electronic display, the input trace such that an axis of the input trace corresponding to relative scan number positions of fluorescent values of the input trace is aligned with an axis for displaying the basecall position indications corresponding to relative scan number positions.

32. The method of claim 31 wherein the axis of the input trace is the same axis as the axis for displaying the basecall position indications.

33. The method of claim 30 further comprising displaying, on the electronic display, a visual indication of a quality value for each of the plurality of basecalls.

34. The method of claim 30 further comprising displaying a visual indication of a quality value for each of the plurality of basecalls wherein the visual indication of the quality value is also used as the basecall position indication by placing the visual indication of the quality value at a location on the electronic display that represents the basecall position.

35. A method of automatically sequencing one or more deoxyribonucleic acid (DNA) molecules of a biological sample, comprising:
 a. using a capillary electrophoresis (CE) genetic analyzer to measure the biological sample to obtain an input trace comprising digital data corresponding to fluorescent values comprising a plurality of scans of the biological sample;
 b. using a trained artificial neural network comprising a plurality of layers including convolutional layers to generate scan labelling probabilities for the plurality of scans; and
 c. determining a basecall sequence comprising a plurality of basecalls for the one or more DNA molecules by decoding the scan labelling probabilities for each of the plurality of scans using a prefix beam search.

36. The method of claim 35, wherein decoding the scan labelling probabilities using the prefix beam search comprises:
 a. initializing an empty basecall sequence as a prefix;
 b. at each scant of the plurality of scans,
  i. extending the prefixes with each of a plurality of extended labels;
  ii. scoring each prefix by incorporating a scan labelling probability of the extended label at the scan t;
  iii. saving an extended candidate subset comprising the K highest scoring prefixes wherein the subset does not exceed a beam width of size K;
  iv. saving the highest scoring prefix at the scan in a candidate subset if the prefix is different from the highest scoring prefix at the previous scan t−1;
  v. assigning the scan to the highest scoring prefix if the prefix is different from the highest scoring prefix at the previous scan t−1;
  vi. returning the highest scoring prefix at the last scan as the final basecall sequence; and
  vii. returning the candidate subset of the top candidates saved at each scan during the prefix beam search.

37. The method of claim 36, wherein the plurality of extended labels comprises pure base labels, mixed base labels, and a blank label.

38. The method of claim 36, further comprising finding a scan range for each basecall and then using the scan range to find a scan position having a peak labelling probability within the scan range.

39. The method of claim 38, wherein finding the scan range and the scan position with the peak labelling probability within the scan range for each basecall comprises:
 a. starting with a first basecall in a final basecall sequence y;
 b. at each basecall $y^i$ of the plurality of basecalls in the final basecall sequence y,
  i. searching the basecall sub-sequence $y^{1\cdots i}$, with the first i basecalls in the basecall sequence yin the candidate subset;
  ii. setting a begin scan of the scan range for the basecall $y^i$ as the scan assigned to the found candidate;
  iii. setting an end scan of the scan range for the basecall $y^i$ by extending the begin scan with the prefixed scan number until the start scan of a next basecall $y^{i+1}$; and
  iv. selecting a scan position for the basecall $y^i$, between the begin scan and the end scan with the peak labelling probability; and
 c. returning the begin and end scans and the scan positions for all basecalls in the final basecall sequence.

40. A method of automatically sequencing one or more deoxyribonucleic acid (DNA) molecules of a biological sample, comprising:
- a. using a capillary electrophoresis (CE) genetic analyzer to measure the biological sample to obtain an input trace comprising digital data corresponding to fluorescent values comprising a plurality of scans of the biological sample;
- b. using a trained artificial neural network comprising a plurality of layers including convolutional layers to generate scan labelling probabilities for the plurality of scans;
- c. determining a basecall sequence comprising a plurality of basecalls for the one or more DNA molecules based on the scan labelling probabilities for each of the plurality of scans; and
- d. determining a quality value for each of the plurality of basecalls by, for a basecall of the plurality of basecalls, using a plurality of feature values derived from scan labelling probabilities corresponding to scans in scan range that includes a scan position of the basecall, the plurality of feature values comprising a peak scan labelling probability of the basecall, a noise-to-signal ratio, a basecall spacing ratio, and a resolution value.

41. The method of claim 40, further comprising using a machine learning algorithm to obtain the quality value using the plurality of feature values.

42. The method of claim 40, wherein the noise-to-signal ratio comprises a ratio of (1) a maximum scan labelling probability from one or more uncalled bases or noise scan labelling probabilities within the local scan window for the basecall, to (2) the scan labelling probability of the called base at a scan position for the basecall.

43. The method of claim 40, wherein the basecall spacing ratio comprises a ratio of a first base spacing value between the basecall and a first neighboring basecall and a second base spacing value between the basecall and a second neighboring basecall.

44. The method of claim 40, wherein the resolution value comprises a ratio of a local base spacing value to a width value of a scan labelling probability peak for the basecall.

45. A method of automatically sequencing one or more deoxyribonucleic acid (DNA) molecules of a biological sample, comprising:
- a. using a capillary electrophoresis (CE) genetic analyzer to measure the biological sample to obtain an input trace comprising digital data corresponding to fluorescent values comprising a plurality of scans of the biological sample;
- b. using a trained artificial neural network comprising a plurality of layers including convolutional layers to generate scan labelling probabilities for the plurality of scans;
- c. determining a basecall sequence comprising a plurality of basecalls for the one or more DNA molecules based on the scan labelling probabilities for each of the plurality of scans;
- d. determining a feature vector for the basecall, the feature vector comprising a plurality of feature values including: a scan labelling probability of the basecall at a basecall scan position, a noise-to-signal ratio, a basecall spacing ratio, and a resolution value;
- e. finding a line having a smallest cut index in a quality value lookup table comprising a plurality of lines wherein each line has (1) a feature vector assigned to a cut comprising a plurality of basecalls, and (2) a quality value corresponding to an empirical error rate of the cut; and
- f. traversing the quality value lookup table in order to assign a quality value corresponding to the line having the smallest cut index to the basecall, where the line having the smallest cut index comprises the line having a feature vector having all feature values greater than or equal to the feature vector for the basecall, or assigning a quality value of zero if no line having the smallest cut index is found.

46. The method of claim 45, wherein the quality value lookup table is constructed by:
- a. initializing a quality value lookup table;
- b. computing a feature vector for each basecall in a quality value training dataset comprising a plurality of samples;
- c. until all remaining cuts are added to the lookup table, grouping the basecalls into a plurality of cuts wherein each cut equalizes a histogram for the feature vector;
- d. computing an empirical error rate for each of the one or more cuts;
- e. adding a cut having the lowest empirical error rate to the quality value lookup table as a next new line comprising a feature vector assigned to the cut and a quality value corresponding to the empirical error rate of the cut;
- f. removing the cut added to the quality value lookup table from the plurality of cuts;
- g. removing all basecalls in the cut added to the quality value lookup table from the remaining cuts; and
- h. repeating steps (c) through (g) until there are no more cuts remaining.

* * * * *